United States Patent

Hemmi et al.

Patent Number: 5,491,132
Date of Patent: Feb. 13, 1996

[54] AMINO ACID DERIVATIVES, A PROCESS FOR THE PREPARATION THEREOF AND PHARMACEUTICAL COMPOSITION COMPRISING THE SAME

[75] Inventors: Keiji Hemmi, Tsukuba; Masahiro Neya, Tsuchiura; Hiroshi Marusawa, Yokohama; Shinya Watanabe, Tsuchiura; Masashi Hashimoto, Toride, all of Japan

[73] Assignee: Fujisawa Pharmaceutical Co., Ltd., Osaka, Japan

[21] Appl. No.: 202,551

[22] Filed: Feb. 28, 1994

Related U.S. Application Data

[63] Continuation of Ser. No. 758,690, Sep. 12, 1991, abandoned.

[30] Foreign Application Priority Data

Sep. 17, 1990 [GB] Great Britain ............................ 9020305
Mar. 15, 1991 [GB] Great Britain ............................ 9105580

[51] Int. Cl.$^6$ ............................ A61K 38/00; C07K 5/00; C07K 7/00; C07K 17/00

[52] U.S. Cl. ............................ 514/18; 530/331; 530/800

[58] Field of Search ...................... 530/331, 800; 514/18

[56] References Cited

U.S. PATENT DOCUMENTS

| | | | |
|---|---|---|---|
| 4,921,855 | 5/1990 | Hemmi et al. | 514/235.8 |
| 4,963,530 | 10/1990 | Hemmi et al. | 514/19 |
| 5,142,048 | 8/1992 | Hemmi et al. | 544/172 |
| 5,223,489 | 6/1993 | Hemmi et al. | 514/19 |
| 5,250,517 | 10/1993 | Branca et al. | 514/18 |
| 5,256,645 | 10/1993 | Branca et al. | 514/18 |

*Primary Examiner*—Jill Warden
*Assistant Examiner*—Sheela J. Huff
*Attorney, Agent, or Firm*—Oblon, Spivak, McClelland, Maier & Neustadt

[57] ABSTRACT

This invention relates to new amino acid derivatives and pharmaceutically acceptable salts thereof, wherein the amino acid derivatives are useful in the treatment and/or prevention of hypertension, heart failure, renal diseases or glaucoma.

11 Claims, No Drawings

AMINO ACID DERIVATIVES, A PROCESS FOR THE PREPARATION THEREOF AND PHARMACEUTICAL COMPOSITION COMPRISING THE SAME

This is a continuation of application Ser. No. 07/758,690, filed on Sep. 12, 1991, now abandoned.

This invention relates to new amino acid derivatives and pharmaceutically acceptable salts thereof.

More particularly, it relates to new amino acid derivatives and pharmaceutically acceptable salts thereof which have inhibitory activities against renin, to a process for the preparation thereof, to a pharmaceutical composition comprising the same and to a method for the treatment and/or prevention of hypertension, heart failure, renal diseases [e.g. renal failure, diabetic nephropathy, glomerulonephritis, pyelonephritis, nephrosis syndorome, Bartter's syndrome, renin-secreting renal tumor, renal edema, hyperuricemia, gout, etc.], glaucoma and the like in human beings or animals. Additionally, the object compound is expected to be useful as a therapeutic agent for dementia.

One object of this invention is to provide new and useful amino acid derivatives and pharmaceutically acceptable salts thereof which possess inhibitory activities against renin, and which are useful as a hypotensor and therapeutic agents on heart failure, renal diseases, glaucoma and the like, especially for oral administration.

Another object of this invention is to provide a process for the preparation of said amino acid derivatives and salts thereof.

A further object of this invention is to provide a pharmaceutical composition comprising, as an active ingredient, said amino acid derivatives and pharmaceutically acceptable salts thereof.

Still further objects of this invention is to provide a therapeutical method for the treatment and/or prevention of hypertension, heart failure, renal diseases, glaucoma and the like.

Some amino acid derivatives having inhibitory activities against renin have been known as described, for example, in European Patent Application Publication Nos. 0172346, 0283970, 0300189 and 0391180 and International Publication No. WO87/04349.

The object amino acid derivatives of this invention are new and can be represented by the following general formula [I]:

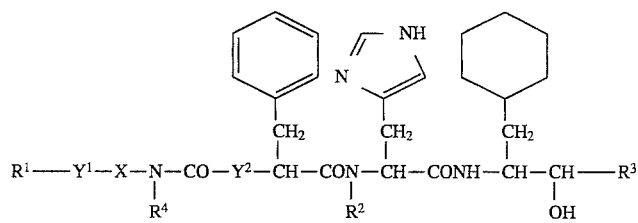

wherein $R^1$ is acyl or a heterocyclic group, $R^2$ is lower alkyl, $R^3$ is lower alkyl which may be substituted with substituent(s) selected from the group consisting of aryl and cyclo(lower)alkyl, $R^4$ is lower alkyl, X is lower alkylene, $Y^1$ is a single bond or

in which $R^5$ is lower alkyl, and $Y^2$ is —NH— or —O—, provided that 1) $R^1$ is morpholinocarbonyl, thiomorpholinocarbonyl or lower alkanoyl and. $R^3$ is isobutyl, 2-ethylbutyl or lower alkyl substituted with substituent(s) selected from the group consisting of aryl and cyclo(lower)alkyl, or $R^1$ is hexahydro-1H-azepin-1-ylcarbonyl, octahydroazocin-1-ylcarbonyl, piperidinocarbonyl, dipropylcarbamoyl or tetrahydroisoquinolylcarbonyl, when $Y^1$ is a single bond and $Y^2$ is —O—; and 2) $R^1$ is morpholinocarbonyl or lower alkanoyl and $R^3$ is isobutyl, 2-ethylbutyl or lower alkyl substituted with substituent(s) selected from the group consisting of aryl and cyclo(lower)alkyl, or $R^1$ is thiomorpholinocarbonyl, hexahydro-1H-azepin-1-ylcarbonyl, octahydroazocin-1-ylcarbonyl, piperidinocarbonyl, dipropylcarbamoyl or tetrahydroisoquinolylcarbonyl, when $Y^1$ is

and $Y^2$ is —O—.

The object compound [I] or its salt can be prepared by a process as illustrated in the following reaction schemes, but preparations of the object compound [I] are not limited to the following process.

Process 1

Step 1

3

-continued
Process 1

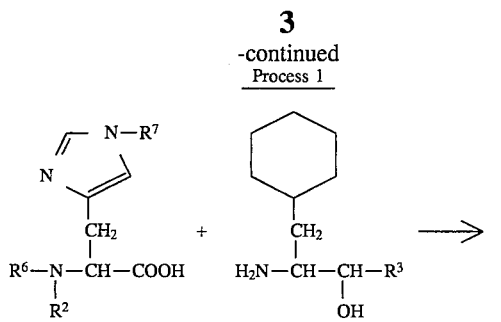

[II]
or its reactive derivative
at the carboxy group or
a salt thereof

[III]
or its reactive derivative
at the amino group or
a salt thereof

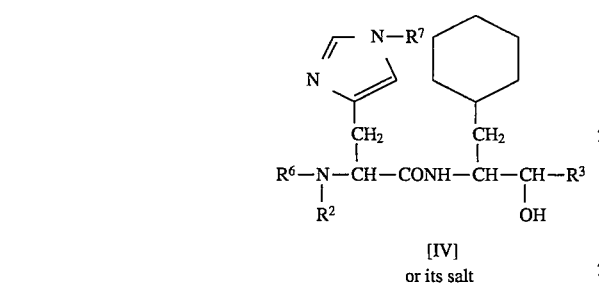

[IV]
or its salt

Step 2

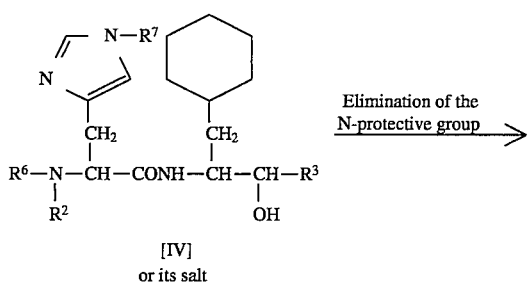

[IV]
or its salt

Elimination of the
N-protective group

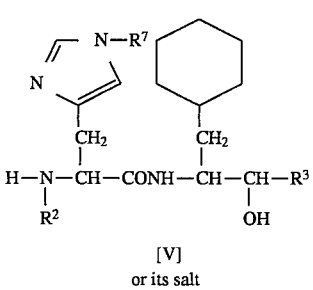

[V]
or its salt

Step 3

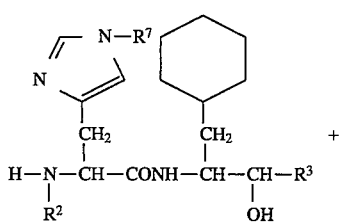

[V]
or its reactive derivative
at the amino group or
a salt thereof

4

-continued
Process 1

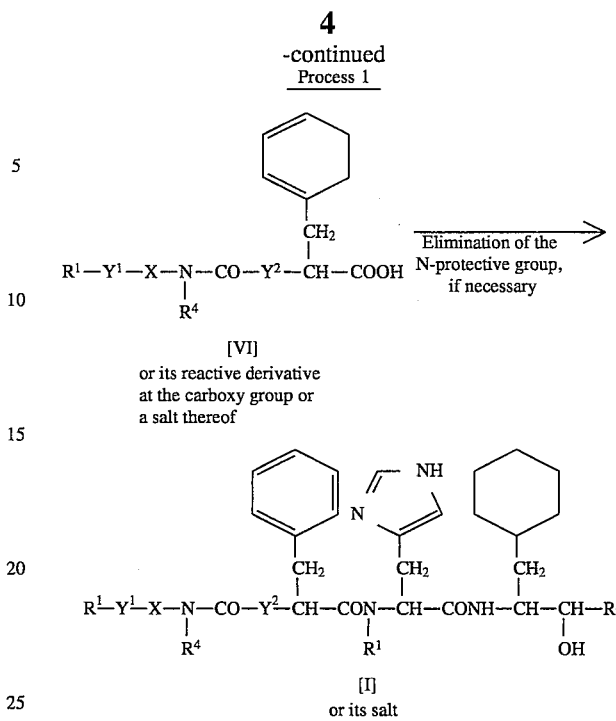

wherein $R^6$ is an N-protective group, $R^7$ is hydrogen or an N-protective group, and $R^1$, $R^2$, $R^3$, $R^4$, X, $Y^1$ and $Y^2$ are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

The lower moiety in the term "cyclo(lower)alkyl" is intended to mean a group having 3 to 6 carbon atoms.

Suitable "lower alkyl" may be a straight or branched one such as methyl, ethyl, propyl, isopropyl, butyl, hexyl, isobutyl, tert-butyl, pentyl, isopentyl, neopentyl, 2-ethylbutyl, and the like.

Suitable "cyclo(lower)alkyl" may be cyclopropyl, cyclobutyl, cyclopentyl or cyclohexyl, in which cyclohexyl is preferred.

Suitable "acyl" may be lower alkanoyl [e.g. formyl, acetyl, propionyl, butyryl, isobutyryl, valeryl, isovaleryl, pivaloyl, 4-methylvaleryl, etc.], mono- or di(lower)alkylamino(lower)alkanoyl [e.g. methylaminoacetyl, methylaminopropionyl, dimethylaminobutyryl, etc.], lower alkoxy(lower)alkanoyl [e.g. methoxyacetyl, methoxypropionyl, ethoxypropionyl, etc.], aroyl [e.g. benzoyl, toluoyl, etc.], cyclo(lower)alkylcarbonyl [e.g. cyclopropylcarbonyl, cyclobutylcarbonyl, cyclopentylcarbonyl, cyclohexylcarbonyl, etc.], amino-protected or unprotected amino acid residue [e.g. glycyl, benzoylglycyl, t-butoxycarbonylglycyl, t-butoxycarbonylleucyl, acetylleucyl, t-butoxycarbonylhistidyl, etc.], carbamoyl, mono- or di(lower)alkylcarbamoyl [e.g. methylcarbamoyl, ethylcarbamoyl, propylcarbamoyl, isopropylcarbamoyl, butylcarbamoyl, pentylcarbamoyl, isobutylcarbamoyl, tert-butylcarbamoyl, dimethylcarbamoyl, diethylcarbamoyl, dipropylcarbamoyl, methylethylcarbamoyl, methylisopropylcarbamoyl, methylisobutylcarbamoyl, etc.], heterocyclic(lower)alkylcarbamoyl [e.g. picolylcarbamoyl, pyridylethylcarbamoyl, thiazolylmethylcarbamoyl, morpholinomethylcarbamoyl, morpholinoethylcarbamoyl, etc.], N-heterocyclic(lower)alkyl-N-lower alkylcarbamoyl [e.g. N-picolyl-N-methylcarbamoyl, N-pyridylethyl-N-methylcarbamoyl, N-morpholinomethyl-N-methylcarbamoyl, N-morpholinoethyl-N-methylcarbamoyl, etc.], ar(lower)alkylcarbamoyl [e.g. benzylcarbamoyl, phenethylcarbamoyl, benzhydrylcarbamoyl, etc.], N-ar(lower)alkyl-N-lower alkylcarbamoyl [e.g. N-benzyl-N-methylcarbamoyl, N-phenethyl-N-methylcarbamoyl, N-phenethyl-N-ethylcarbamoyl, etc.], N-aryl-N-lower alkylcarbamoyl [e.g. N-phenyl-N-methylcarbamoyl, etc.], lower alkylcarbonyl(lower)alkylcarbamoyl [e.g. methoxycarbonylmethylcarbamoyl, ethoxycarbonylmethylcarbamoyl, ethoxycarbonylethylcarbamoyl, etc.], lower alkoxy(lower)alkylcarbamoyl [e.g. methoxymethylcarbamoyl, methoxyethylcarbamoyl, ethoxypropylcarbamoyl, etc.], aroylcarbamoyl [e.g. benzoylcarbamoyl, toluoylcarbamoyl, etc.], heterocycliccarbamoyl [e.g. pyridylcarbamoyl, morpholinocarbamoyl, thiazolylcarbamoyl, etc.], N-heterocyclic-N-lower alkylcarbamoyl [e.g. N-pyridyl-N-methylcarbamoyl, N-thiazolyl-N-methylcarbamoyl, etc.], heterocycliccarbonyl, preferably N-containing heterocyclic-N-ylcarbonyl which may be substituted with lower alkyl [e.g. morpholinocarbonyl, thiomorpholinocarbonyl, piperidinocarbonyl, 4-methyl-1-piperazinylcarbonyl, 1,2,3,6-tetrahydro-1-pyridylcarbonyl, hexahydro-1H-azepin-1-ylcarbonyl, octahydroazocin-1-ylcarbonyl, 1,2,3,4-tetrahydro-2-isoquinolylcarbonyl, etc.], lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], mono(or di or tri)halo(lower)alkoxycarbonyl [e.g. iodoethoxycarbonyl, dichloroethoxycarbonyl, trichloroethoxycarbonyl, trifluoromenhoxycarbonyl, etc.], hydroxy(lower)alkoxycarbonyl [e.g. hydroxymethoxycarbonyl, hydroxyethoxycarbonyl, hydroxypropoxycarbonyl, hydroxybutoxycarbonyl, etc.], ar(lower)alkoxycarbonyl, [e.g. benzyloxycarbonyl, phenethyloxycarbonyl, 4-nitrobenzyloxycarbonyl, trityloxycarbonyl, benzhydryloxycarbonyl, etc.], lower alkenyloxycarbonyl [e.g. vinyloxycarbonyl, allyloxycarbonyl, etc.], lower alkanoyl(lower)alkoxycarbonyl [e.g. acetylmethoxycarbonyl, propionylmethoxycarbonyl, acetylethoxycarbonyl, etc.], lower alkylsulfonyl [e.g. mesyl, ethylsulfonyl, propylsulfonyl, isopropylsulfonyl, butylsulfonyl, isobutylsulfonyl, tert-butylsulfonyl, pentylsulfonyl, hexylsulfonyl, etc.], arylsulfonyl [e.g. phenylsulfonyl, tosyl, etc.] or the like.

Suitable "aryl" may be phenyl, naphthyl, phenyl substituted with lower alkyl (e.g. tolyl, xylyl, mesityl, cumenyl, etc.) and the like, in which phenyl is preferred.

Suitable "heterocyclic group" may be one containing at least one hetero atom selected from nitrogen, sulfur and oxygen atom, and may include saturated or unsaturated, monocyclic or polycyclic heterocyclic group, and a preferable heterocyclic group may be N-containing heterocyclic group such as unsaturated 3 to 6-membered heteromonocyclic group containing 1 to 4 nitrogen atoms, for example, pyrrolyl, pyrrolinyl, imiazolyl, pyrazolyl, pyridyl, pyrimidinyl, pyrazinyl, pyridazinyl, triazolyl [e.g., 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.; saturated 3 to 8-membered heteromonocyclic group containing 1 to 4 nitrogen atoms [e.g. pyrrolidinyl, imidazolidinyl, piperidino, piperazinyl, hexahydroazepinyl, octahydroazocinyl, etc.]; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], tetrahydroisoquinolyl, etc.; unsaturated 3 to 6-membered heteromonocyclic group containing an oxygen atom, for example, pyranyl, furyl, etc.;

unsaturated 3 to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.], etc.;

saturated 3 to 6-membered heteromonocyclic group containing 1 to 2 oxygen atoms and 1 to 3 nitrogen atoms [e.g. morpholinyl, etc.];

unsaturated condensed heterocyclic group containing 1 to 2 oxygen atoms and 1 to 3 nitrogen atoms [e.g. benzoxazolyl, benzoxadiazolyl, etc.];

unsaturated 3 to 6-membered heteromonocyclic group containing 1 to 2 sulfur atoms and 1 to 3 nitrogen atoms, for example, thiazolyl, thiadiazolyl [e.g. 1,2,4-thiadiazolyl, 1,3, 4-thiadiazolyl, 1,2,5-thiadiazolyl, etc.], etc.;

saturated 3 to 6-membered heteromonocyclic group containing 1 to 2 sulfur atoms and 1 to 3 nitrogen atoms [e.g., thiazolidinyl, thiomorpholinyl, etc.];

unsaturated condensed heterocyclic group containing 1 to 2 sulfur atoms and 1 to 3 nitrogen atoms [e.g., benzothiazolyl, benzothiadiazolyl, etc.] and the like.

Pyridyl is a preferable heterocyclic group.

Preferable "lower alkyl substituted with substituent(s) selected from the group consisting of aryl and cyclo(lower)alkyl" are diaryl(lower)alkyl, cyclo(lower)alkyl(lower)alkyl and dicyclo(lower)alkyl(lower)alkyl, in which more preferable ones are diphenylethyl, cyclohexylmethyl and dicyclohexylethyl.

Suitable "lower alkylene" may be a straight or branched one such as methylene, ethylene, trimethylene, tetramethylene, pentamethylene, hexamethylene, propylene, methylmethylene, ethylmethylene, propylmethylene, and the like, in which $C_1$-$C_4$ alkylene are more preferable and methylene, ethylene, trimethylene, tetramethylene and methylmethylene are most preferable.

Suitable "N-protective group" may be substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.], substituted or unsubstituted aralkyloxycarbonyl [e.g. benzyloxycarbonyl, p-nitrobenzyloxycarbonyl, etc.], substituted or unsubstituted arenesulfonyl [e.g. benzenesulfonyl, tosyl, etc.], nitrophenylsulfenyl, aralkyl [e.g. trityl, benzyl, etc.] or the like.

Preferable compounds [I] are ones which have thiomorpholinocarbonyl, hexahydro-1H-azepin-1-ylcarbonyl, piperidinocarbonyl or lower alkanoyl for $R^1$, lower alkyl for $R^2$, lower alkyl for $R^3$, lower alkyl for $R^4$, lower alkylene for X,

(wherein $R^5$ is lower alkyl) for $Y^1$ and —NH— for $Y^2$;

morpholinocarbonyl, thiomorpholinocarbonyl, hexahydro-1H-azepin-1-ylcarbonyl, octahydroazocin-1-ylcarbonyl, piperidinocarbonyl or lower alkanoyl for $R^1$, lower alkyl for $R^2$, lower alkyl for $R^3$ lower alkyl for $R^4$, lower alkylene for X, a single bond or

(wherein $R^5$ is lower alkyl) for $Y^1$ and —NH— for $Y^2$ provided that $R^3$ is isobutyl or 2-ethylbutyl when $R^1$ is morpholinocarbonyl and $Y^1$ is

and acyl (more preferably morpholinocarbonyl, thiomorpholinocarbonyl, hexahydro-1H-azepin-1-ylcarbonyl, octahydroazocin-1-ylcarbonyl, piperidinocarbonyl, lower alkanoyl, dipropylcarbamoyl or tetrahydroisoquinolylcarbonyl) or a heterocyclic group (more preferably pyridyl) for $R^1$, lower alkyl for $R^2$, lower alkyl which may be substituted with substituent(s) selected from the group consisting of aryl (more preferably phenyl) and cyclo(lower)alkyl (more preferably cyclohexyl) for $R^3$, lower alkyl for $R^4$, lower alkylene for X, a single bond or

(wherein $R^5$ is lower alkyl) for $Y^1$ and —NH— or —O— for $Y^2$ provided that 1) $R^1$ is morpholinocarbonyl, thiomorpholinocarbonyl or lower alkanoyl and $R^3$ is isobutyl, 2-ethylbutyl or lower alkyl substituted with substituent(s) selected from the group consisting of aryl (more preferably phenyl) and cyclo(lower)alkyl (more preferably cyclohexyl), or $R^1$ is hexahydro-1H-azepin-1-ylcarbonyl, octahydroazocin-1-ylcarbonyl, piperidinocarbonyl, dipropylcarbamoyl or tetrahydroisoquinolylcarbonyl, when $Y^1$ is a single bond and $Y^2$ is —O—; and 2) $R^1$ is morpholinocarbonyl or lower alkanoyl and $R^3$ is isobutyl, 2-ethylbutyl or lower alkyl substituted with substituent(s) selected from the group consisting of aryl (more preferably phenyl) and cyclo(lower)alkyl (more preferably cyclohexyl), or $R^1$ is thiomorpholinocarbonyl, hexahydro-1H-azepin-1-ylcarbonyl, octahydroazocin-1-ylcarbonyl, piperidinocarbonyl, dipropylcarbamoyl or tetrahydroisoquinolylcarbonyl, when $Y^1$ is

and $Y^2$ is —O—; in which a more preferable one is morpholinocarbonyl or thiomorpholinocarbonyl for $R^1$, lower alkyl for $R^2$, lower alkyl for $R^3$, lower alkyl for $R^4$, lower alkylene for X, a single bond or

(wherein $R^5$ is lower alkyl) for $Y^1$ and —NH— for $Y^2$; and most preferable is morpholinocarbonyl for $R^1$, lower alkyl for $R^2$, lower alkyl for $R^3$, lower alkyl for $R^4$, lower alkylene for X,

(wherein $R^5$ is lower alkyl) for $Y^1$ and —NH— for $Y^2$.

Suitable pharmaceutically acceptable salts of the object compounds [I] are conventional non-toxic salts and include an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. aspartic acid salt, glutamic acid salt, etc.], or the like.

The process for preparing the object compounds [I] is explained in detail in the following.

Process 1

Step 1

The compound [IV] or its salt can be prepared by reacting a compound [II] or its reactive derivative at the carboxy group or a salt thereof with a compound [III] or its reactive derivative at the amino group or a salt thereof.

Suitable salts of the compound [IV] can be referred to the ones as exemplified for the compound [I].

A suitable reactive derivative at the carboxy group of the compound [II] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl $[(CH_3)_2N^+=CH—]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected according to the kind of the compound [II] to be used.

Suitable salts of the compound [II] and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], or the like, and an acid addition salt as exemplified for the compound [I].

Suitable reactive derivative at the amino group of the compound [III] may include Schiff's base type imino or its tautomeric enamine type isomer formed by the reaction of the compound [III] with a carbonyl compound such as aldehyde, ketone or the like; a silyl derivative formed by the reaction of the compound [III] with a silyl compound such as bis(trimethylsilyl)acetamide, mono(trimethylsilyl)acetamide, bis(trimethylsilyl)urea or the like; a derivative formed by reaction of the compound [III] with phosphorus trichloride or phosgene, and the like.

Suitable salts of the compound [III] and its reactive derivative can be referred to the ones as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

In this reaction, when the compound [II] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-( 2-methylimidazole); pentamethyleneketene-N-cyclohexylimine; diphenylketene-N-cyclohexylimine; ethoxyacetylene; 1-alkoxy-1-chloroethylene; trialkyl phosphite, ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt;

1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, oxalyl chloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out in a range of cooling conditions to warming conditions.

Step 2

The compound [V] or its salt can be prepared by subjecting a compound [IV] or its salt to elimination reaction of the N-protective group.

Suitable salts of the compound [V] can be referred to the ones as exemplified for the compound [I].

This reaction is carried out in accordance with a conventional method such as hydrolysis, reduction or the like.

The hydrolysis is preferably carried out in the presence of a base or an acid including Lewis acid.

A suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]-non- 5-ene, 1,4-diazabicyclo[2.2.2]octane, 1,8-diazabicyclo[5.4.0]undec-7-ene, or the like.

Suitable acids may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can also be used as the solvent. The reaction temperature is not critical and the reaction is usually carried out under cooling conditions to heating conditions.

The reduction method applicable for the elimination reaction may include chemical reduction and catalytic reduction.

Suitable reducing agents to be used in chemical reduction are a combination of a metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.]. Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in the case that the above-mentioned acids to be used in chemical reduction are liquid, they can also be used as a solvent. Further, a suitable solvent to be used in catalytic reduction may be the above-mentioned solvent, and other conventional solvents such as diethyl ether, dioxane, tetrahydrofuran, etc. or a mixture thereof.

The reaction temperature of this reduction is not critical and the reaction is usually carried out under cooling to heating.

Step 3

The object compound [I] or its salt can be prepared by reacting a compound [V] or its reactive derivative at the amino group or a salt thereof with a compound [VI] or its reactive derivative at the carboxy group or a salt thereof, and if necessary, eliminating the N-protective group.

Suitable salts of the compound [VI] can be referred a base salt as exemplified for the compound [II].

This reaction can be carried out in substantially the same manner as Step 1, and therefore the reaction mode and reaction conditions [e.g. reactive derivatives, condensing agents, solvents, reaction temperature, etc.] of this reaction are to be referred to those as explained in Step 1.

In case the imidazole group of the compound [V] is protected, the object compound [I] can be prepared by further eliminating the N-protective group of the reaction product of the compound [V] with the compound [VI].

This elimination reaction can be carried out in substantially the same manner as Step 2 in this process, and therefore the reaction mode and reaction conditions [e.g. bases, acids, reducing agents, catalysts, solvents, reaction temperature, etc.] of this reaction are to be referred to those as explained in Step 2 in this process.

Among the starting compounds [VI], some are new and can be prepared by processes as illustrated in the following reaction schemes.

Process A

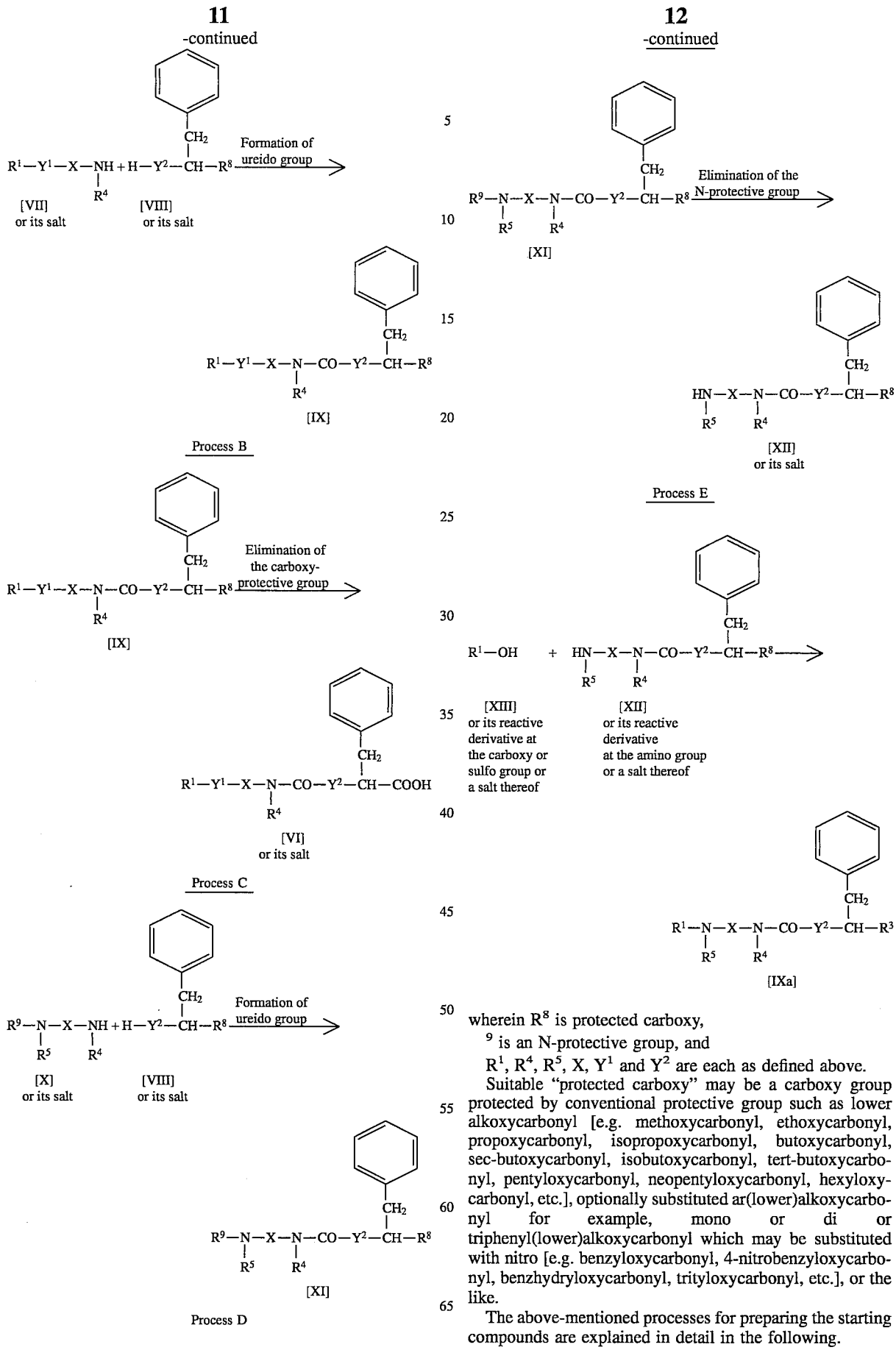

wherein $R^8$ is protected carboxy,
$R^9$ is an N-protective group, and
$R^1$, $R^4$, $R^5$, X, $Y^1$ and $Y^2$ are each as defined above.

Suitable "protected carboxy" may be a carboxy group protected by conventional protective group such as lower alkoxycarbonyl [e.g. methoxycarbonyl, ethoxycarbonyl, propoxycarbonyl, isopropoxycarbonyl, butoxycarbonyl, sec-butoxycarbonyl, isobutoxycarbonyl, tert-butoxycarbonyl, pentyloxycarbonyl, neopentyloxycarbonyl, hexyloxycarbonyl, etc.], optionally substituted ar(lower)alkoxycarbonyl for example, mono or di or triphenyl(lower)alkoxycarbonyl which may be substituted with nitro [e.g. benzyloxycarbonyl, 4-nitrobenzyloxycarbonyl, benzhydryloxycarbonyl, trityloxycarbonyl, etc.], or the like.

The above-mentioned processes for preparing the starting compounds are explained in detail in the following.

Process A

The compound [IX] can be prepared by subjecting a compound [VII] or its salt and a compound [VIII] or its salt to an ureido group formation reaction.

Suitable salts of the compounds [VII] and [VIII] can be referred to the ones as exemplified for the compound [I].

This reaction is carried out in the presence of a reagent which introduces a carbonyl group such as phosgene, haloformate compound [e.g. ethyl chloroformate, trichloromethyl chloroformate, etc.], N,N'-carbonyldiimidazole, metal carbonyl compounds [e.g. cobalt carbonyl, manganese carbonyl, etc.], a combination of carbon monoxide and catalysts such as palladium chloride, etc., or the like.

This reaction is usually carried out in a solvent such as dioxane, tetrahydrofuran, benzene, toluene, chloroform, methylene chloride, N,N-dimethylformamide or any other organic solvent which does not adversely influence the reaction.

The reaction temperature is not critical and the reaction is usually carried out under cooling to heating.

Process B

The compound [VI] or its salt can be prepared by subjecting a compound [IX] to a carboxy-protective group elimination reaction.

Suitable salts of the compound [VI] can be referred to a base salt as exemplified for the compound [II].

This reaction can be carried out in substantially the same manner as Step 2 in Process 1, and therefore the reaction mode and reaction conditions [e.g. bases, acids, reducing agents, catalysts, solvents, reaction temperature, etc.] of this reaction are to be referred to those as explained in Step 2 in Process 1.

Process C

The compound [XI] can be prepared by subjecting a compound [VIII] or its salt and a compound [X] or its salt to an ureido group formation reaction.

This reaction can be carried out in substantially the same manner as Process A, and therefore the reaction mode and reaction conditions [e.g. carbonyl group-introducing reagents, solvents, reaction temperature, etc.] of this reaction are to be referred to those as explained in Process A.

Process D

The compound [XII] or its said can be prepared by subjecting a compound [XI] or its salt to an N-protective group elimination reaction.

Suitable salts of the compound [XII] can be referred to the ones as exemplified for the compound [I].

This reaction can be carried out in substantially the same manner as Step 2 in Process 1, and therefore the reaction mode and reaction conditions [e.g. bases, acids, reducing agents, catalysts, solvents, reaction temperature, etc.] of this reaction are to be referred to those as explained in Step 2 in Process 1.

Process E

The compound [IXa] can be prepared by reacting a compound [XII] or its reactive derivative at the amino group or a salt thereof with a compound [XIII] or its reactive derivative at the carboxy or sulfo group or a salt thereof.

Suitable salts of the compound [XII] can be referred to the ones as exemplified for the compound [I].

Suitable salts of the compound [XIII] can be referred to a base salt as exemplified for the compound [II].

This reaction can be carried out in substantially the same manner as Step 1 in Process 1, and therefore the reaction mode and reaction conditions [e.g. reactive derivatives, condensing agents, solvents, reaction temperature, etc.] of this reaction are to be referred to those as explained in Step 1 in Process 1.

The compounds obtained by the above processes can be isolated and purified by a conventional method such as pulverization, recrystallization, column chromatography, reprecipitation, or the like.

It is to be noted that the compound [I] and the other compounds may include one or more stereoisomers due to asymmetric carbon atoms, and all of such isomers and mixture thereof are included within the scope of this invention.

The object compounds [I] and pharmaceutically acceptable salts thereof possess strong inhibitory activities against renin, and are useful as a hypotensor and a therapeutic agent on heart failure, renal diseases [e.g. renal failure, diabetic nephropathy, glomerulonephritis, pyelonephritis, nephrosis syndrome, Bartter's syndrome, renin-secreting renal tumor, renal edema, hyperuricemia, gout, etc.], glaucoma and the like, especially for oral administration.

For therapeutic purposes, the compounds [I] and pharmaceutically acceptable salts thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral or external (topical) administration. The pharmaceutical preparation may be capsule, tablet, dragee, suppository, granule, solution, lotion, suspension, emulsion, ointment, gel, or the like. If desired, there may be included in these preparations, auxiliary substances, stabilizing agents, wetting or emulsifying agents, buffers and other commonly used additives.

While the dosage of the compounds [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

In order to illustrate the usefulness of the object compound [I], the pharmacological test data of some representative compounds of the compound [I] are shown in the following.

Test Compounds (1) (2S,3S)-2-[N$^\alpha$-[N-[N-Methyl-N-{2-(N-thiomorpholinocarbonyl-N-methylamino)ethyl} -aminocarbonyl]-L-phenylalanyl]-N$^\alpha$-methyl-L-histidyl] amino-1-cyclohexyl-3-hydroxy-6-methylheptane hydrochloride (2) (2S,3S)-2-[N$^\alpha$-[N-[N-Methyl-N-{2-(N-piperidinocarbonyl-N-methylamino)ethyl} -aminocarbonyl]-L-phenylalanyl]-N$^\alpha$-methyl-L-histidyl] amino-1-cyclohexyl-3-hydroxy-6-methylheptane hydrochloride (3) (2S,3S)-2-[N$^\alpha$-[N-[N-{2-[N-(Hexahydro-1H-azepin-1-ylcarbonyl)-N-methylamino]ethyl}-N-methylaminocarbonyl]-L-phenylalanyl]-N $^\alpha$-methyl-L-histidyl]-amino- 1-cyclohexyl-3-hydroxy-6-methylheptane hydrochloride (4) (2S,3S)-2-[N$^\alpha$-[N-Methyl-N-{2-(N-morpholinocarbonyl-N-methylamino)ethyl} aminocarbonyl]-L-phenylalanyl]-N$^\alpha$-methyl-L-histidyl]-amino- 1-cyclohexyl-3-hydroxy-5-methylhexane hydrochloride (5) 2S,3S)-2-[N$^\alpha$-[N-[N-Methyl-N-{2-(N-thiomorpholinocarbonyl-N-methylamino)ethyl} -aminocarbonyl]-L-phenylalanyl]-N$^\alpha$-methyl-L-histidyl]-amino- 1-cyclohexyl-3-hydroxy-5-methylhexane hydrochloride (6) (2S,3S)-2-[N$^\alpha$[N-[N-Methyl-N-{2-(N-morpholinocarbonyl-N-methylamino)ethyl} aminocarbonyl]L-phenylalanyl]-N$^\alpha$-methyl-L-histidyl]amino-1-cyclohexyl- 3-hydroxy-5-ethylheptane hydrochloride (7) (2S,3S)-2-[N$^\alpha$[N-[N-Methyl-N-(2-morpholinocarbonylethyl)-aminocarbonyl] -L-phenylalanyl]-N$^\alpha$-methyl-L-histidyl]amino- 1-cyclohexyl-3-hydroxy-5-ethylheptane hydrochloride (8) (2S,3S)-2-[N$^\alpha$-[N-[N-[2-(N-Dipropylcarbamoyl-N-methylamino)ethyl] -N-methylaminocarbonyl]-L-phenylalanyl]-N$^\alpha$-methyl-L-histidyl]amino- 1-cyclohexyl-3-hydroxy-6-methylheptane hydrochloride (9) (2S,3S)-2-[N$^\alpha$-[N-[N-[2-[N-(1,2,3,4-Tetrahydro-2-isoquinolylcarbonyl)-N-methylamino]ethyl]N-methylaminocarbonyl] -L-phenylalanyl]-N$^\alpha$-methyl-L-histidyl]amino-1-cyclohexyl-3-hydroxy-6-methylheptane hydrochloride

(10) (2S,3S)-2-[N$^\alpha$-[N-[N-(2-Pyridyl)ethyl-N-methylaminocarbonyl] -L-phenylalanyl]-N$^\alpha$-methyl-L-histidyl] amino-1-cyclohexyl-3-hydroxy-6-methylheptane dihydrochloride

(11) (2S,3S)-2-[N$^\alpha$-[N-[N-Methyl-N-{2-(N-thiomorpholinocarbonyl-N-methylamino)ethyl} aminocarbonyl]-L-phenylalanyl]-N$^\alpha$-methyl-L-histidyl]amino-1, 4-dicyclohexyl- 3-hydroxybutane hydrochloride

(12) (2S,3S)-2-[N$^\alpha$-[(2S)-2-[N-[ 2-(N-Methyl-N-morpholinocarbonylamino)ethyl] ]-N-methylaminocarbonyl]-oxy- 3-phenylpropionyl]-N$^\alpha$-methyl-L-histidyl] amino-1-cyclohexyl- 3-hydroxy-5-methylhexane hydrochloride

(13) (2S,3S)-2-[N$^\alpha$-[(2S)-2-(N-Methyl-N-thiomorpholinocarbonylamino)ethyl] -N-methylaminocarbonyl] oxy- 3-phenylpropionyl]-N$^\alpha$-methyl-L-histidyl] amino-1-cyclohexyl-3-hydroxy-5-ethylheptane hydrochloride Test Method Human plasma was collected from male volunteers pretreated with no drugs and used as a pool. Disodium salt of ethylenediaminetetraacetic acid (EDTA) was used as the anticoagulant. Plasma renin activity was measured as the rate of angiotensin I (Ang I) formation after incubation (37° C.) of the endogenous renin and angiotensinogen in plasma at pH 6.0. The incubation mixture contained 250 μl of plasma, 5 μl of (phenylmethyl)sulfonyl fluoride, 30 μl of buffer (sodium, potassium-phosphate, pH 6.0), and 15 μl of an appropriate concentration of test compound in 50% ethyl alcohol-water vehicle. The Ang I formed after 90 minutes of incubation was measured by radioimmunoassay (RIA) which was carried out with a commercial kit, RENIN.RIA-BEAD (Trademark: manufactured by Dainabot Co., Ltd.). Samples were incubated in duplicate and each tube was measured in duplicate in the RIA. Percentage inhibition of plasma renin activity was calculated by comparing the amount of Ang I produced with and without a test compound. The concentration of test compound that inhibited plasma renin activity by 50% (IC$_{50}$) was determined by Probit method.

| Test Results | |
|---|---|
| Test Compound | IC$_{50}$ (M) |
| (1) | $2.9 \times 10^{-10}$ |
| (2) | $1.0 \times 10^{-9}$ |
| (4) | $4.7 \times 10^{-10}$ |
| (5) | $7.9 \times 10^{-11}$ |
| (6) | $3.0 \times 10^{-10}$ |
| (7) | $1.7 \times 10^{-9}$ |
| (8) | $3.8 \times 10^{-10}$ |
| (9) | $3.9 \times 10^{-9}$ |

| Test Results | |
|---|---|
| Test Compound | IC$_{50}$ (M) |
| (10) | $9.6 \times 10^{-9}$ |
| (11) | $7.2 \times 10^{-10}$ |
| (12) | $3.1 \times 10^{-9}$ |
| (13) | $3.9 \times 10^{-9}$ |

The following Preparations and Examples are given for the purpose of illustrating preferable preparations of the object compounds [I], and preparations of said compounds are not limited to the following Preparations and Examples.

In the following Preparations and Examples, Kieselgel 60F 254 (Trademark: manufactured by Merck & Co.) (thickness: 0.25 mm) was used as TLC plate.

Preparation 1

To a solution of L-phenylalanine benzyl ester hydrochloride (9.46 g) in dry toluene (150 ml) was added trichloromethyl chloroformate (3.94 ml). After being stirred at 130° C. for 5 hours, the solution was concentrated in vacuo. The residue was dissolved in dry tetrahydrofuran (100 ml) and a solution of N-tert-butoxycarbonyl-N,N'-dimethylethylenediamine (5.55 g) in dry tetrahydrofuran (10 ml) was added to the solution at ambient temperature. The mixture was stirred at the same temperature for 2 hours. After evaporation of the solvent, the residue was dissolved in ethyl acetate (500 ml) and the solution was washed with 5% hydrochloric acid, saturated sodium bicarbonate solution, and brine successively, dried over anhydrous magnesium sulfate, and concentrated under reduced pressure. The residue was purified with silica gel column chromatography (n-hexane:ethyl acetate, 1:1, V/V) to give N-[N-[2-(N-tert-butoxycarbonyl-N-methylamino)ethyl] -N-methylaminocarbonyl] -L-phenylalanine benzyl ester (11.5 g) as an oil.

Rf: 0.37 (n-hexane:ethyl acetate, 1:1, V/V)

Preparation 2

N-[N-[2-(N-tert-Butoxycarbonyl-N-methylamino)ethyl]-N-methylaminocarbonyl] -L-phenylalanine benzyl ester (11 g was dissolved in a solution of 4M hydrogen chloride in ethyl acetate (200 ml) under ice-bath cooling. After being stirred at the same temperature for 30 minutes, the solution was concentrated in vacuo to give N-[N-[2-(N-methylamino)ethyl]-N-methylaminocarbonyl] -L-phenylalanine benzyl ester hydrochloride (10 g) as an oil.

Rf: 0.36 (10% methanol in chloroform)

Preparation 3

To a solution of N-[N-[2-(N-methylamino)ethyl]-N-methylaminocarbonyl] -L-phenylalanine benzyl ester hydrochloride (1.62 g) and triethylamine (1.12 ml) in methylene chloride (20 ml) was added a solution of N-thiomorpholinocarbonyl chloride (0.66 g) at ambient temperature. After being stirred an the same temperature for 2 hours, the solution was concentrated in vacuo. The residue was dissolved in ethyl acetate (50 ml) and the solution was washed with 5% hydrochloric acid, saturated sodium bicarbonate solution and brine successively, dried over anhydrous magnesium sulfate, and concentrated under reduced pressure. The residue was purified with silica gel column chromatography (n-hexane:ethyl acetate, 1:1, V/V) to give N-[N-[2-(N-thiomorpholinocarbonyl-N-methylamino)ethyl] -N-methylaminocarbonyl]-L-phenylalanine benzyl ester (1.51 g) as an oil.

Rf: 0.27 (ethyl acetate)

Preparation 4

The following compounds were obtained according to a similar manner to that of Preparation 3.

(1) N-[N-{2-[N-(Hexahydro-1H-azepin-1-ylcarbonyl)-N-methylamino]ethyl}-N-methylaminocarbonyl]-L-phenylalanine benzyl ester Rf: 0.43 (ethyl acetate)

(2) N-[N-[2-(N-Piperidinocarbonyl-N-methylamino)ethyl]-N-methylaminocarbonyl] -L-phenylalanine benzyl ester Rf: 0.43 (ethyl acetate)

(3) N-[N-[2-(N-Isobutyryl-N-methylamino)ethyl]-N-methylaminocarbonyl]-L-phenylalanine benzyl ester Rf: 0.47 (ethyl acetate)

(4) N-[N-{2-[N-(Octahydroazocin-1-ylcarbonyl)-N-methylamino] ethyl}-N-methylaminocarbonyl]-L-phenylalanine benzyl ester Rf: 0.31 (ethyl acetate)

(5) N-[N-[2-(N-Dipropylcarbamoyl-N-methylamino)ethyl]-N-methylaminocarbonyl] -L-phenylalanine benzyl ester Rf: 0.39 (ethyl acetate)

(6) N-[N-[2-[N-(1,2,3,4-Tetrahydro-2-isoquinolyl-carbonyl)-N-methylaminocarbonyl] ethyl]-N-methylamino -L-phenylalanine benzyl ester Rf: 0.31 (ethyl acetate)

Preparation 5

To a solution of N-[N-[2-(N-thiomorpholinocarbonyl-N-methylamino)ethyl] -N-methylaminocarbonyl]-L-phenylalanine benzyl ester (1.50 g) in methanol (30 ml) was added in 1N sodium hydroxide aqueous solution (6 ml) at ambient temperature. After being stirred for 3 hours at the same temperature, the solution was concentrated in vacuo. The residue was dissolved in ethyl acetate (50 ml) and the solution was washed with 5% hydrochloric acid and brine successively, dried over anhydrous magnesium sulfate, and concentrated under reduced pressure to give N-[N-[2-(N-thiomorpholinocarbonyl-N-methylamino)ethyl] -N-methylaminocarbonyl]-L-phenylalanine (1.14 g) as an oil. Rf : 0.31 ( chloroform:methanol:acetic acid, 16:1:1, V/V)

Preparation 6

A solution of N-[N-{2-[N-(hexahydro-1H-azepin-1-ylcarbonyl)-N-methylamino] ethyl}-N-methylaminocarbonyl]-L-phenylalanine benzyl ester (1.46 g) in methanol (20 ml) was hydrogenated over 10% palladium on carbon (146 mg) at 3 atmospheric pressure of hydrogen gas for 1 hour at ambient temperature. The solution was filtered and concentrated in vacuo to give N-[N-{2-[N-(hexahydro-1H-azepin-1-ylcarbonyl)-N-methylamino]ethyl}-N-methylaminocarbonyl] -L-phenylalanine (1.28 g) as an oil. Rf: 0.35 (chloroform:methanol:acetic acid, 16:1:1, V/V)

Preparation 7

The following compounds were obtained according to a similar manner to that of Preparation 6.

(1) N-[N-[2-(N-Piperidinocarbonyl-N-methylamino)ethyl]-N-methylaminocarbonyl] -L-phenylalanine Rf: 0.36 (chloroform:methanol:acetic acid, 16:1:1, V/V)

(2) N-[N-[2-(N-Isobutyryl-N-methylamino)ethyl]-N-methylaminocarbonyl] -L-phenylalanine Rf: 0.28 (chloroform:methanol:acetic acid, 16:1:1, V/V)

(3) N-[N-{2-[N-(Octahydroazocin-1-ylcarbonyl)-N-methylamino]ethyl}-N-methylaminocarbonyl]-L-phenylalanine Rf: 0.25 (chloroform:methanol, 5:1, V/V)

(4) N-[N-[2-(N-Dipropylcarbamoyl-N-methylamino)ethyl]-N-methylaminocarbonyl] -L-phenylalanine Rf: 0.29 (chloroform:methanol, 5:1, V/V)

(5) N-[N-[2-[N-(1,2,3,4-Tetrahydro-2-isoquinolylcarbonyl)-N-methylamino]ethyl]-N-methylaminocarbonyl] -L-phenylalanine Rf: 0.27 (chloroform:methanol, 10:1, V/V)

(6) N-[N-(2-Pyridyl)ethyl-N-methylaminocarbonyl]-L-phenylalanine Rf: 0.53 (chloroform:methanol:acetic acid, 8:2:1, V/V)

(7) N-[N-(2-Morpholinocarbonylethyl)-N-methylaminocarbonyl] -L-phenylalanine Rf: 0.16 (10% methanol in chloroform)

(8) N-[N-{2-(N-Morpholinocarbonyl-N-methylamino)ethyl}-N-methylaminocarbonyl] -L-phenylalanine Rf: 0.43 (chloroform:methanol:acetic acid, 8:1:1, V/V)

Preparation 8

To a solution of N-t-butoxycarbonyl-L-cyclohexylalaninal (1.36 g) in dry tetrahydrofuran (20 ml) which was cooled to −78° C., was added dropwise a solution of isobutylmagnesium bromide prepared from isobutyl bromide (5.32 g) and magnesium (1.04 g) in dry tetrahdrufuran (25 ml). After the addition was complete, the reaction mixture was allowed to warm to ambient temperature for 2.5 hours and was poured into saturated aqueous ammonium chloride (50 ml). The resulting slurry was extracted with ethyl acetate (30 ml×2), and the combined ethyl acetate extract was washed with water, dried over magnesium sulfate, and evaporated. Chromatography of the residual oil on silica gel (100 g) column, eluting with 10% ethyl acetate in n-hexane, afforded (2S,3S)-2-t-butoxycarbonylamino-1-cyclohexyl-3-hydroxy-5-methylhexane (396 mg) as an oil. Rf: 0.42 (benzene:ethyl acetate, 4:1, V/V)

Preparation 9

The following compounds were obtained according to a similar manner to that of Preparation 8.

(1) (2S,3S)-2-t-Butoxycarbonylamino-1-cyclohexyl-3-hydroxy- 5-ethylheptane Rf: 0.46 (ethyl acetate:benzene, 1:4, V/V)

(2) (2S,3S)-2-t-Butoxycarbonylamino-1-cyclohexyl-3-hydroxy- 5,5-dimethylhexane Rf: 0.46 (benzene:ethyl acetate, 4:1, V/V)

(3) (2S,3S)-2-t-Butoxycarbonylamino-1,4-dicyclohexyl-3-hydroxybutane Rf: 0.46 (benzene:ethyl acetate, 4:1, V/V)

(4) (2S,3S)-2-t-Butoxycarbonylamino-1-cyclohexyl-5,5-diphenyl- 3-hydroxypentane Rf: 0.52 (n-hexane:ethyl acetate, 2:1, V/V)

Preparation 10

A solution of (2S,3S)-2-t-butoxycarbonylamino-1-cyclohexyl- 3-hydroxy-5-methylhexane (120 mg) in trifluoroacetic acid (3 ml) was stirred at 0° C. for 30 minutes. After evaporation of the solvent, the residue was dissolved in ethyl acetate (10 ml). The solution was washed with saturated sodium bicarbonate solution and saturated sodium chloride solution, dried over magnesium sulfate, and evaporated in vacuo to give (2S,3S)-2-amino-1-cyclohexyl-3-hydroxy-5-methylhexane (82 mg) as an oil. Rf: 0.30 (chloroform: methanol: acetic acid, 16:1:1, V/V)

Preparation 11

The following compounds were obtained according to a similar manner to that of Preparation 10.

(1) (2S,3 S)-2-Amino-1-cyclohexyl-3-hydroxy-5-ethylheptane Rf: 0.30 ( chloroform:methanol:acetic acid, 16:1:1, V/V)

(2) (2S,3S)-2-Amino-1-cyclohexyl-3-hydroxy-5,5-dimethylhexane Rf: 0.13 (chloroform:methanol, 10:1, V/V)

(3) (2S,3S)-2-Amino-1,4-dicyclohexyl-3-hydroxybutane Rf: 0.33 (chloroform:methanol:acetic acid, 16:1:1, V/V)

(4) (2S,3S)-2-Amino-3-hydroxy-1,5,5-tricyclohexylpentane Rf: 0.15 (benzene:ethyl acetate:acetic acid, 20:20:1, V/V)

(5) (2S,3S)-2-Amino-1-cyclohexyl-5,5-diphenyl-3-hydroxypentane Rf: 0.05 (benzene:ethyl acetate:acetic acid, 20:20:1, V/V)

Preparation 12

To a solution of $N^\alpha$-t-butoxycarbonyl-$N^\alpha$-methyl-$N^{im}$-tosyl-L-histidine (195 mg) and (2S,3S)-2-amino-1-cyclohexyl-3-hydroxy-5-methylhexane (82 mg) in dry methylene chloride (10 ml) which was cooled at 0° C., was added 1-ethyl-3-(3-dimethylaminopropyl)carbodiimide (72 mg). The mixture was stirred at 0° C. for 3 hours. After evaporation of the solvent, the residue was dissolved in ethyl acetate (20 ml) and the solution was washed with 10% citric acid solution, saturated sodium bicarbonate solution, and water, dried over magnesium sulfate, and concentrated under reduced pressure. The residue was purified with silica gel column chromatography (ethyl acetate:n-hexane, 2:3, V/V, as eluent) to give (2S,3S)-2-($N^\alpha$-t-butoxycarbonyl-$N^\alpha$-methyl-$N^{im}$-tosyl-L-histidyl)amino-1-cyclohexyl-3-hydroxy-5-methylhexane (166 mg) as an amorphous powder. Rf: 0.29 (ethyl acetate:n-hexane, 3:2, V/V)

Preparation 13

The following compounds were obtained according to a similar manner to that of Preparation 12.

(1) (2S,3S)-2-($N^\alpha$-t-Butoxycarbonyl-$N^\alpha$-methyl-$N^{im}$-tosyl-L-histidyl)amino- 1-cyclohexyl-3-hydroxy-5-ethylheptane Rf: 0.36 (ethyl acetate:n-hexane, 3: 2, V/V)

(2) (2S,3S)-2-($N^\alpha$-t-Butoxycarbonyl-$N^\alpha$-methyl-$N^{im}$-tosyl-L-histidyl)amino-1-cyclohexyl-3-hydroxy-5,5-dimethylhexane Rf: 0.33 (ethyl acetate:n-hexane, 3:2, V/V)

(3) (2S,3S)-2-($N^\alpha$-t-Butoxycarbonyl-$N^\alpha$-methyl-$N^{im}$-tosyl-L-histidyl)amino- 1,4-dicyclohexyl-3-hydroxybutane Rf: 0.35 (ethyl acetate:n-hexane, 3:2, V/V)

(4) (2S,3S)-2-($N^\alpha$-t-Butoxycarbonyl-$N^\alpha$-methyl-$N^{im}$-tosyl-L-histidyl)amino-3-hydroxy-1,5,5-tricyclohexylpentane Rf: 0.64 (n-hexane:ethyl acetate, 1:1, V/V)

(5) (2S,3S)-2-($N^\alpha$t-Butoxycarbonyl-$N^\alpha$methyl-$N^{im}$-tosyl-L-histidyl)amino- 1-cyclohexyl-5,5-diphenyl-3-hydroxypentane Rf: 0.5 (n-hexane:ethyl acetate, 1:1, V/V)

Preparation 14

A solution of (2S,3S)-2-($N^\alpha$-t-butoxycarbonyl-$N^\alpha$-methyl-$N^{im}$-tosyl-L-histidyl)amino-1-cyclohexyl-3-hydroxy-5-methylhexane (160 mg) in trifluoroacetic acid (5 ml) was stirred at 0° C. for 2 hours. After concentration of the mixture in vacuo, the residue was dissolved in ethyl acetate (20 mi). The solution was washed with saturated sodium bicarbonate solution and saturated sodium chloride solution, dried over magnesium sulfate, and concentrated in vacuo to give (2S,3S)-2-($N^\alpha$-methyl-$N^{im}$-tosyl-L-histidyl)amino-1-cyclohexyl-3-hydroxy-5-methylhexane (134 mg) as an amorphous powder. Rf: 0.44 (chloroform:methanol, 10:1, V/V)

Preparation 15

The following compounds were obtained according to a similar manner to that of Preparation 14.

(1) (2S,3S)-2-($N^\alpha$-Methyl-$N^{im}$-tosyl-L-histidyl)amino-1-cyclohexyl- 3-hydroxy-5-ethylheptane Rf: 0.48 (chloroform:methanol 10:1, V/V)

(2) (2S,3S)-2-($N^\alpha$-Methyl-$N^{im}$-tosyl-L-histidyl)amino-1-cyclohexyl- 3-hydroxy-5,5-dimethylhexane Rf: 0.55 (chloroform:methanol, 10:1, V/V)

(3) (2S,3S)-2-($N^\alpha$-Methyl-$N^{im}$-tosyl-L-histidyl)amino-1, 4-dicyclohexyl- 3-hydroxybutane Rf: 0.44 (chloroform:methanol, 10:1, V/V)

(4) (2S,3S)-2-($N^\alpha$-Methyl-$N^{im}$-tosyl-L-histidyl)amino-3-hydroxy- 1,5,5-tricyclohexylpentane Rf: 0.71 (chloroform:methanol, 9:1, V/V)

(5) (2S,3S)-2-($N^\alpha$-Methyl-$N^{im}$-tosyl-L-histidyl)amino-1-cyclohexyl-5,5-diphenyl-3-hydroxypentane Rf: 0.68 (chloroform:methanol, 9:1, V/V)

Preparation 16

N-t-Butoxycarbonyl-N,N'-dimethylethylenediamine (200 mg) was added to a solution of thiomorpholinocarbonyl chloride (228 mg) and triethylamine (123 mg) in methylene chloride (10 ml) which was cooled at 0° C. The mixture was stirred at ambient temperature for 20 minutes and the solvent was evaporated in vacuo. The residue was dissolved in ethyl acetate and the solution was washed with 0.6N hydrochloric acid, water, saturated sodium bicarbonate solution, and saturated sodium chloride solution successively, dried over magnesium sulfate, and concentrated under reduced pressure to give N-t-butoxycarbonyl-N'-thiomorpholinocarbonyl-N,N'-dimethylethylenediamine (376 mg) as an oil. Rf: 0.43 (chloroform:methanol, 10:1, V/V)

Preparation 17

N-t-Butoxycarbonyl-N'-thiomorpholinocarbonyl-N,N'-dimethylethylenediamine (4.92 g) was dissolved in a solution of 4N hydrogen chloride in ethyl acetate (60 ml) under ice-bath cooling. After being stirred at ambient temperature for 30 minutes, the solution was concentrated in vacuo to give N-thiomorpholinocarbonyl-N,N'-dimethylethylenediamine hydrochloride (3.93 g) as an oil. Rf: 0.25 (chloroform:methanol:acetic acid, 8:1:1, V/V)

Preparation 18

A solution of di-t-butyl dicarbonate (3.57 g) in methylene chloride (20 mi) was added dropwise to a solution of 2-(2-aminoethyl)pyridine (2 g) in methylene chloride (40 ml). The mixture was stirred at ambient temperature for 2 hours and the solvent was evaporated in vacuo. The residue was dissolved in ethyl acetate (60 ml), washed with saturated sodium bicarbonate solution and saturated sodium chloride solution successively, dried over magnesium sulfate, and concentrated under reduced pressure. The residual solid was washed with n-hexane to give 2-[2-(N-t-butoxycarbonylamino)ethyl]pyridine (3.29 g) as yellow crystal. Rf: 0.52 (chloroform:methanol, 10:1, V/V)

Preparation 19

A solution of 2-[2-(N-t-butoxycarbonylamino)ethyl]-pyridine (1.8 g) in N,N-dimethylformamide (7 ml) was added dropwise to a suspension of sodium hydride (0.39 g) in N,N-dimethylformamide (7 ml) which was cooled at 0° C. The mixture was stirred at 0° C. for 1 hour. Methyl iodide (1.4 g) was added to this solution at the same temperature. After stirring at 0° C. for 1 hour and at ambient temperature for 2 hours, the mixture was poured into ice water, saturated with sodium chloride, and extracted with ethyl acetate 3 times. The combined organic layer was washed with saturated sodium thiosulfate, saturated sodium bicarbonate and saturated sodium chloride successively, dried over magnesium sulfate, and concentrated under reduced pressure. The residue was purified with silica gel chromatography (ethyl acetate:n-hexane, 3:1, V/V, as eluent) to give 2-[2-(N-t-butoxycarbonyl-N-methylamino)ethyl]-pyridine (1.47 g) as an oil.

Preparation 20

To a solution of N-thiomorpholinocarbonyl-N,N'-dimethylethylenediamine (3.93 g) and triethylamine (1.57 g) in ethyl acetate (200 ml), which was cooled to 0° C., was added a solution of (1S)-1-benzyloxycarbonyl-2-phenylethyl isocyanate (3.63 g) prepared by reacting L-phenylalanine benzyl ester with trichloromethylchloroformate. After being stirred at ambient temperature for 30 minutes, the solution was washed with 5% hydrochloric acid, saturated sodium bicarbonate solution and brine successively, dried over anhydrous magnesium sulfate, and concentrated under reduced pressure. The residue was purified with silica gel column chromatography (ethyl acetane:n-hexane, 1:1 to 1:0, V/V) to give N-[N-[2-N-thiomorpholinocarbonyl-N-methylamino)ethyl] -N-methylaminocarbonyl]-L-phenylalanine benzyl ester (4.52 g) as an oil. Rf: 0.27 (ethyl acetate)

Preparation 21

A solution of 4N-hydrogen chloride in ethyl acetate (5 ml) was added to 2-[2-(N-t-butoxycarbonyl-N-methylamino)ethyl] pyridine at 0° C. The solution was stirred at 0° C. for 1 hour and concentrated under reduced pressure. The residue was dissolved in methylene chloride (10 ml). Triethylamine (304 mg) and (1S)-1-benzyloxycarbonyl- 2-phenylethyl isocyanate (281 mg) prepared by reacting L-phenylalanine benzyl ester with trichloromethylchloroformate was added to this solution at 0° C. The solution was stirred at the same temperature for 1 hour and the solvent was evaporated in vacuo. The residue was dissolved in ethyl acetate and the solution was washed with 10% citric acid aqueous solution, saturated sodium bicarbonate solution, and saturated sodium chloride solution successively, dried over magnesium sulfate, and concentrated under reduced pressure to give N-[N-(2-pyridyl)ethyl-N-methylaminocarbonyl]-L-phenylalanine benzyl ester (400 mg) as an oil. Rf: 0.50 ( chloroform:methanol, 20: 1, V/V)

Preparation 22

To a solution of benzyl (2S)-2-[N-[2-(N-t-butoxycarbonyl-N-methylamino)ethyl] -N-methylaminocarbonyl] oxy-3-phenylpropionate (5.40 g) in ethyl acetate (50 ml) which was cooled at 0° C. was added 4N hydrogen chloride solution in ethyl acetate (50 ml). The solution was stirred at 0° C. for 1 hour and the solvent was evaporated in vacuo to give benzyl (2S)-2-[N-[2-(N-methylamino)ethyl] -N-methylaminocarbonyl]oxy-3-phenylpropionate hydrochloride (4.70 g) as a solid. Rf: 0.23 (chloroform:methanol, 10:1, V/V)

Preparation 23

To a solution of benzyl (2S)-2-[N-[2-(N-methylamino)ethyl] -N-methylaminocarbonyl]oxy-3-phenylpropionate hydrochloride (300 mg) and triethylamine (153 mg) in methylene chloride (5 ml) which was cooled at 0° C. was added thiomorpholinocarbonyl chloride (129 mg). The solution was stirred at ambient temperature for 2 hours and the solvent was evaporated in vacuo. The residue was dissolved in ethyl acetate, washed with 0.5N hydrochloric acid, saturated sodium bicarbonate solution and saturated sodium chloride solution successively, dried over magnesium sulfate, and concentrated under reduced pressure. The residue was purified with silica gel column chromatography (ethyl acetate:n-hexane, 3:1, V/V, as eluent) to give benzyl (2S)-2-[N-[2-(N-methyl-N-thiomorpholinocarbonylamino)ethyl] -N-methylaminocarbonyl]-oxy- 3-phenylpropionate (287 mg) as an oil. Rf: 0.46 (ethyl acetate)

Preparation 24

The following compound was obtained according to a similar manner to that of Preparation 23.

Benzyl (2S)-2-[N-[2-{N-(hexahydro-1H-azepin-1-ylcarbonyl)-N-methylamino}ethyl] -N-methylaminocarbonyl]-oxy- 3-phenylpropionate Rf: 0.42 (ethyl acetate)

Preparation 25

To a solution of benzyl (2S)-2-[N-[2-(N-methyl-N-thiomorpholinocarbonylamino)ethyl] -N-methylaminocarbonyl]-oxy- 3-phenylpropionate (0.95 g) and ammonium formate (2 g) was added 10% palladium on carbon (0.5 g) and the solution was stirred at ambient temperature for 1 hour. After filtration of the catalyst, the solvent was evaporated in vacuo. The residue was dissolved in ethyl acetate, washed with water, dried over magnesium sulfate, and concentrated under reduced pressure to give (2S)-2-[N-[2-(N-methyl-N-thiomorpholinocarbonylamino)ethyl] -N-methylaminocarbonyl]-oxy- 3-phenylpropionic acid (548 mg) as an oil. Rf: 0.56 (chloroform:methanol:acetic acid, 16:1:1, V/V)

Preparation 26

A solution of benzyl (2S)-2-[N-[2-{N-(hexahydro-1H-azepin-1-ylcarbonyl)-N-methylamino}ethyl]-N-methylaminocarbonyl] oxy-3-phenylpropionate (1.43 g) in methanol (20 ml) was hydrogenated over 10% palladium on carbon (0.2 g) at 3 atmospheric pressure of hydrogen gas for 1 hour at ambient temperature. The solution was filtered and concentrated in vacuo to give (2S)-2-[N-[2-{N-(hexahydro-1H-azepin-1-ylcarbonyl)-N-methylamino} ethyl]-N-methylaminocarbonyl]oxy-3-phenylpropionic acid (1.09 g) as an oil. Rf: 0.44 (chloroform:methanol:acetic acid, 16:1:1, V/V)

Preparation 27

A solution of (2S,3S)-2-t-butoxycarbonylamino-1-cyclohexyl- 5,5-diphenyl-3-hydroxypentane (0.74 g) in acetic acid (50 ml) was hydrogenated over platinum oxide (0.2 g) at 3 atmospheric pressure of hydrogen gas for 2 hours at 37° C. The solution was filtered and concentrated in vacuo to give (2S,3S)-2-t-butoxycarbonylamino-3-hydroxy- 1,5,5-tricyclohexylpentane (753 mg) as an oil. Rf: 0.72 (n-hexane:ethyl acetate, 2:1, V/V)

Preparation 28

To a solution of L-phenylalanine benzyl ester p-toluenesulfonic acid salt (6.41 g) in dry toluene (100 ml) was added triethylamine (1.52 g) and trichloromethyl chloroformate (0.92 mi). After the mixture was stirred at 80° C. for 30 minutes, the solution was concentrated in vacuo. The residue was dissolved in dry tetrahydrofuran (100 ml) and a mixture of N-isobutyryl-N,N'-dimethylethylenediamine trifluoroacetic acid salt (4.08 g) and, triethylamine (1.52 g) in dry tetrahydrofuran (40 ml) was added thereto at 0° C. The mixture was stirred at the same temperature for 3 hours. After evaporation of the solvent, the residue was dissolved in ethyl acetate (150 ml) and the solution was washed with 5% hydrochloric acid, saturated sodium bicarbonate solution, and water successively, dried over magnesium sulfate, and concentrated under reduced pressure. The residue was purified with silica gel column chromatography (n-hexane:ethyl acetate, 1:2, V/V) to give N-[N-{2-(N-isobutyryl-N-methylamino)ethyl}-N-methylaminocarbonyl]-L-phenylalanine benzyl ester (2.29 g) as an oil. Rf: 0.48 (ethyl acetate)

Preparation 29

The following Compounds were obtained according to a similar manner to that of Preparation 28.

(1) N-[N-(2-Morpholinocarbonylethyl)-N-methylaminocarbonyl] -L-phenylalanine benzyl ester (1.10 g) was obtained from L-phenylalanine benzyl ester p-toluenesulfonic acid salt (3.42 g), 4-[3-(N-methylamino)propionyl] morpholine trifluoroacetic acid salt (2.29 g) and trichloromethyl chloroformate (0.49 ml). Rf : 0.30 (ethyl acetate)

(2) N-[N-2-(N-Morpholinocarbonyl-N-methylamino)ethyl}-N-methylaminocarbonyl] -L-phenylalanine benzyl ester (4.00 g) was obtained from L-phenylalanine benzyl ester p-toluenesulfonic acid salt (7.09 g), N-morpholinocarbonyl-N,N'-dimethylethylenediamine trifluoroacetic acid salt (5.00 g) and trichloromethyl chloroformate (0.92 ml). Rf: 0.56 (ethyl acetate)

EXAMPLE 1

To a solution of N-[N-[2-(N-thiomorpholinocarbonyl-N-methylamino)ethyl] -N-methylaminocarbonyl]-L-phenylalanine (292 mg) and (2S,3S)-2-(N$^\alpha$-methyl-N$^{im}$-tosyl-L-histidyl)amino- 1-cyclohexyl-3-hydroxy-6-methylheptane (346 mg) in methylene chloride (7 ml), which was cooled to 0°

C., was added 1-ethyl-3-(3-dimethylaminopropyl)carbodiimide hydrochloride (150 mg). After being stirred for 5 hours at the same temperature, the solution was concentrated in vacuo. The residue was dissolved in ethyl acetate (20 ml) and the solution was washed with 5% hydrochloric acid, saturated sodium bicarbonate solution and brine successively, dried over anhydrous magnesium sulfate, and concentrated under reduced pressure. After the residue was dissolved in N,N-dimethylformamide (10 ml), pyridine hydrochloride (751 mg) was added to the solution at ambient temperature. The mixture was stirred at the same temperature for 2 hours. After evaporation of the solvent, the residue was dissolved in ethyl acetate (20 ml). The solution was washed with brine, 1M sodium bicarbonate solution and brine successively, dried over anhydrous magnesium sulfate, and concentrated under reduced pressure. The residue was purified with silica gel thin layer chromatography (10% methanol in chloroform) to give (2S,3S)-2-[N$^\alpha$-[N-[N-methyl-N-{2-(N-thiomorpholinocarbonyl-N-methylamino)ethyl} aminocarbonyl]-L-phenylalanyl] -N$^\alpha$-methyl-L-histidyl]amino-1-cyclohexyl-3-hydroxy- 6-methylheptane (300 mg) as an amorphous powder. Rf: 0.38 (10% methanol in chloroform) FAB-MS: 769 (M+H)$^+$

EXAMPLE 2

The following compounds were obtained according to a similar manner to that of Example 1.

(1) (2S,3S)-2-[N$^\alpha$-[N[N-{2-[N-(Hexahydro-1H-azepin-1 -ylcarbonyl)-N-methylamino]ethyl}-N-methylaminocarbonyl] -L-phenylalanyl]-N$^\alpha$-methyl-L-histidyl] amino- 1-cyclohexyl-3-hydroxy-6-methylheptane Rf: 0.30 (10% methanol in chloroform) FAB-MS: 765 (M+H)$^+$ (2) (2S,3S)-2-[N$^\alpha$-[N-[N-Methyl-N-{2-(N-piperidinocarbonyl-N-methylamino)ethyl} aminocarbonyl]-L-phenylalanyl] -N$^\alpha$-methyl-L-histidyl]amino-1-cyclohexyl-3-hydroxy-6-methylheptane Rf: 0.40 (10% methanol in chloroform) FAB-MS: 751 (M+H)$^+$ (3) (2S,3S)-2-[N$^\alpha$-[N-[N-{2-(N-isobutyryl-N-methylamino)ethyl}-N-methylaminocarbonyl] -L-phenylalanyl]-N$^\alpha$-methyl-L-histidyl] amino-1-cyclohexyl-3-hydroxy-6-methylheptane Rf: 0.37 (10% methanol in chloroform) FAB-MS: 710 (M+H)$^+$ (4) (2S,3S)-2-[N$^\alpha$-[N-[N-Methyl-N-{2-(N-morpholinocarbonyl-N-methylamino)ethyl} aminocarbonyl]-L-phenylalanyl]-N$^\alpha$-methyl-L-histidyl]amino-1-cyclohexyl- 3-hydroxy-5-methylhexane Rf: 0.33 (10% methanol in chloroform) FAB-MS: 739 (M+H)$^+$ (5) (2S,3S)-2-[N$^\alpha$-[N-[N-Methyl-N-{2-(N-thiomorpholinocarbonyl-N-methylamino)ethyl} aminocarbonyl]-L-phenylalanyl] -N$^\alpha$-methyl-L-histidyl]amino-1-cyclohexyl- 3-hydroxy-5-methylhexane Rf: 0.36 (chloroform:methanol, 10:1, V/V) FAB-MS: 755 (M+H)$^+$ (6) (2S,3S)-2-[N$^\alpha$-[N-[N-{2-N-(Hexahydro-1H-azepin-1-ylcarbonyl)-N-methylami ethyl}-N-methylaminocarbonyl] -L-phenylalanyl]-N$^\alpha$-methyl-L-histidyl]amino-1-cyclohexyl-3-hydroxy-5-methylhexane Rf: 0.53 (10% methanol in chloroform) FAB-MS: 751 (M+H)$^+$ (7) (2S,3S)-2-[N$^\alpha$-[N-[N-{2-[N-(Octahydroazocin-1-ylcarbonyl)-N-methylamino]ethyl}-N-methylaminocarbonyl] -L-phenylalanyl]-N$^\alpha$-methyl-L-histidyl]-amino- 1-cyclohexyl-3-hydroxy-5-methylhexane Rf : 0.54 (104 methanol in chloroform) FAB-MS : 765 (M+H)$^+$ (8) (2S,3S)-2-[N$^\alpha$-[N-[N-{2-(N-isobutyryl-N-methylamino)ethyl} -N-methylaminocarbonyl]-L-phenylalanyl]-N$^\alpha$-methyl-L-histidyl] amino-1-cyclohexyl-3-hydroxy-5-methylhexane Rf: 0.64 (10% methanol in chloroform) FAB-MS: 696 (M+H)$^+$ (9) (2S,3S)-2-[N$^\alpha$-[N-[N-Methyl-N-{2-(N-thiomorpholinocarbonyl-N-methylamino)ethyl} aminocarbonyl]-L-phenylalanyl]-N$^\alpha$-methyl-L-histidyl]amino- 1-cyclohexyl-3-hydroxy-5-ethylheptane Rf: 0.40 (chloroform:methanol, 10:1, V/V) FAB-MS: 783 (M+H)$^+$

(10) (2S,3S)-2-[N$^\alpha$-[N-[N-Methyl-N-{2-(N-morpholinocarbonyl-N-methylamino)ethyl} -aminocarbonyl]-L-phenylalanyl]-N$^\alpha$-methyl-L-histidyl]-amino- 1-cyclohexyl-3-hydroxy-5-ethylheptane Rf: 0.34 (chloroform:methanol, 10:1, V/V) FAB-MS: 767 (M+H)$^+$

(11) (2S,3S)-2-[N$^\alpha$-[N-[N-{2-(N-Isobutyryl-N-methylamino)ethyl} -N-methylaminocarbonyl]-L-phenylalanyl]-N$^\alpha$-methyl-L-histidyl] amino-1-cyclohexyl-3-hydroxy-5-ethylheptane Rf: 0.36 (chloroform:methanol, 10:1, V/V) FAB-MS: 724 (M+H)$^+$

(12) (2S,3S)-2-[N$^\alpha$-[N-[N-{2-[N-(Hexahydro-1H-azepin- 1-ylcarbonyl)-N-methylamino]ethyl}-N-methylaminocarbonyl] -L-phenylalanyl]-N$^\alpha$-methyl-L-histidyl]-amino- 1-cyclohexyl-3-hydroxy-5-ethylheptane Rf: 0.42 (chloroform:methanol, 10:1, V/V) FAB-MS: 779 (M+H)$^+$

(13) (2S,3S)-2-[N$^\alpha$-[N-[N-{2-[N-(Octahydroazocin-1-ylcarbonyl)-N-methylamino] ethyl}-N-methylaminocarbonyl] -L-phenylalanyl]-N$^\alpha$-methyl-L-histidyl]-amino- 1-cyclohexyl-3-hydroxy-5-ethylheptane Rf: 0.43 (chloroform:methanol, 10:1, V/V) FAB-MS : 793 (M+H)$^+$

(14) (2S,3S)-2-[N$^\alpha$-[N-[N-Methyl-N-{2-(N-thiomorpholino-carbonyl-N-methylamino)ethyl}aminocarbonyl]-L-phenylalanyl] -N$^\alpha$-methyl-L-histidyl]amino-1-cyclohexyl- 3-hydroxy-5,5-dimethylhexane Rf: 0.41 (chloroform:methanol, 10:1, V/V) FAB-MS: 769 (M+H)$^+$

(15) (2S,3S)-2-[N$^\alpha$-[N-[N-Methyl-N-(2-morpholinocarbonylethyl)aminocarbonyl] -L-phenylalanyl]-N$^\alpha$-methyl-L-histidyl] amino-1-cyclohexyl-3-hydroxy-5-ethylheptane Rf: 0..37 (chloroform:methanol:acetic acid, 8:1:1, V/V) FAB-MS: 738 (M+H)$^+$

(16) (2S,3S)-2-[N$^\alpha$-[N-[N-Methyl-N-(2-morpholinocarbonylethyl)aminocarbonyl] -L-phenylalanyl]-N$^\alpha$-methyl-L-histidyl] amino-1-cyclohexyl-3-hydroxy-5-methylhexane Rf: 0.33 (chloroform:methanol:acetic acid, 8:1:1, FAB-MS: 710 (M+H)$^+$

(17) (2S,3S)-2-[N$^\alpha$-[N-[N-{2-[N-(Octahydroazocin-1-ylcarbonyl)-N-methylamino] ethyl}-N-methylaminocarbonyl] -L-phenylalanyl]-N$^\alpha$-methyl-L-histidyl]-amino- 1-cyclohexy1-3-hydroxy-6-methylheptane Rf: 0.47 (chloroform:methanol, 10:1, V/V) FAB-MS: 779 (M+H)$^+$

(18) (2S,3S)-2-[N$^\alpha$-[N-[N-[2-(N-Dipropylcarbamoyl-N-methylamino)ethyl] -N-methylaminocarbonyl]-L-phenylalanyl] -N$^\alpha$-methyl-L-histidyl]amino-1-cyclohexyl-3-hydroxy-6-methylheptane Rf: 0.44 (chloroform:methanol, 10:1, V/V)

(19) (2S ,3S)-2-[N$^\alpha$-[N-[N-[2-N-(1,2,3,4-Tetrahydro-2-isoquinolylcarbonyl)-N-methylamino] ethyl]-N-methylaminocarbonyl]-L-phenylalanyl]-N$^\alpha$-methyl-L-histidyl] amino-1-cyclohexyl-3-hydroxy-6-methylheptane Rf: 0.43 (chloroform:methanol, 10:1, V/V)

(20) (2S, 3S)-2-[N$^\alpha$-[N-[N-(2-Pyridyl)ethyl-N-methylaminocarbonyl] -L-phenylalanyl]-N$^\alpha$-methyl-L-histidyl]amino-1-cyclohexyl-3-hydroxy-6-methylheptane Rf: 0.35 (chloroform:methanol, 10:1, V/V)

(21) (2S, 3S)-2-[N$^\alpha$-[N-[N-Methyl-N-{2-(N-thiomorpholinocarbonyl-N-methylamino)ethyl}aminocarbonyl-L-phenylalanyl]-N$^\alpha$-methyl-L-histidyl]amino-1,4-dicyclohexyl-3-hydroxybutane Rf: 0.38 (chloroform:methanol, 10:1, V/V)

(22) (2S,3S)-2-[N$^\alpha$-[N-[N-Methyl-N-{2-(N-thiomorpholinocarbonyl-N-methylamino)ethyl}aminocarbonyl]-L-phenylalanyl] -N$^\alpha$-methyl-L-histidyl]amino-3-hydroxy-1,5,5-tricyclohexylpentane Rf: 0.5 (chloroform:methanol, 9:1, V/V)

(23) (2S,3S)-2-[N$^\alpha$-[N-[N-Methyl-N-{2-(N-thiomorpholinocarbonyl-N-methylamino)ethyl} aminocarbonyl]-L-phenylalanyl] -N$^\alpha$-methyl-L-histidyl]amino-1-cyclohexyl- 5,5-diphenyl-3-hydroxypentane Rf : 0.4 (chloroform:methanol, 9:1, V/V)

EXAMPLE 3

To a solution of (2S,3S)-2-[N$^\alpha$-[N-[N-methyl-N-{2 -(N-thiomorpholinocarbonyl-N-methylamino)ethyl} aminocarbonyl]-L-phenylalanyl] -N$^\alpha$-methyl-L-histidyl] amino-1-cyclohexyl-3-hydroxy- 6-methylheptane (300 mg) in ethanol (3 ml), which was cooled to 0° C., was added a solution of 4M hydrogen chloride in ethyl acetate (0.100 ml). After being stirred at the same temperature for 10 minutes, the solution was concentrated in vacuo to give (2S,3S)-2-[N$^\alpha$-[N-[N-methyl-{2-(N-thiomorpholinocarbonyl-N-methylamino)ethyl}aminocarbonyl] -L-phenylalanyl]-N$^\alpha$-methyl-L-histidyl]amino-1-cyclohexyl- 3-hydroxy-6-methylheptane hydrochloride (310 mg) as an amorphous powder. Rf: 0.38 (10% methanol in chloroform)

EXAMPLE 4

The following compounds were obtained according to a similar manner to that of Example 3.

(1) (2S,3S)-2-[N$^\alpha$-[N-[N-{2-(N-(Hexahydro-1H-azepin-1 -ylcarbonyl)-N-methylamino)ethyl}-N-methylaminocarbonyl] -L-phenylalanyl]-N$^\alpha$-methyl-L-histidyl] amino-1-cyclohexyl-3-hydroxy-6-methylheptane hydrochloride. Rf: 0.30 (10% methanol in chloroform)

(2) (2S,3S)-2-[N$^\alpha$-[N-[N-Methyl-N-{2-(N-piperidinocarbonyl-N-methylamino)ethyl)}aminocarbonyl]-L-phenylalanyl] -N$^\alpha$-methyl-L-histidyl]amino- 1-cyclohexyl-3-hydroxy-6-methylheptane hydrochloride. Rf: 0.40 (10% methanol in chloroform)

(3) (2S,3S)-2-[N$^\alpha$-[N-[N-{2-(N-Isobutyryl-N-methylamino)ethyl} -N-methylaminocarbonyl]-L-phenylalanyl]-N$^{60}$ -methyl-L-histidyl] amino-1-cyclohexyl-3-hydroxy-6-methylheptane hydrochloride. Rf: 0.37 (10% methanol in chloroform)

(4) (2S,3S)-2-[N$^\alpha$-[N-[N-Methyl-N-{2-(N-morpholinocarbonyl-N-methylamino)ethyl}aminocarbonyl]-L-phenylalanyl] -N$^\alpha$-methyl-L-histidyl]amino-1-cyclohexyl- 3-hydroxy-5-methylhexane hydrochloride Rf: 0 33 (10% methanol in chloroform)

(5) (2S,3S)-2-[N$^\alpha$-[N-[N-Methyl-N-{2-(N-thiomorpholinocarbonyl-N-methylamino)ethyl} aminocarbonyl]-L-phenylalanyl]-N$^\alpha$-methyl-L-histidyl]aminocyclohexyl-3-hydroxy-5-methylhexane hydrochloride Rf: 0.36 (chloroform:methanol, 10:1, V/V)

(6) (2S,3S)-2-[N$^\alpha$-[N-[N-{2-[N-(Hexahydro-1H-azepin-1 -ylcarbonyl)-N-methylamino]ethyl}-N-methylaminocarbonyl] -L-phenylalanyl]-N$^\alpha$-methyl-L-histidyl]-amino- 1-cyclohexyl-3-hydroxy-5-methylhexane hydrochloride Rf: 0.53 (10% methanol in chloroform)

(7) (2S,3S)-2-[N$^\alpha$-[N-[N-{2-[N-(Octahydroazocin-1-ylcarbonyl)-N-methylamino] ethyl}-N-methylaminocarbonyl] -L-phenylalanyl]-N$^\alpha$-methyl-L-histidyl]-amino- 1-cyclohexyl-3-hydroxy-5-methylhexane hydrochloride Rf: 0.54 (10% methanol in chloroform)

(8) (2S,3S)-2-[N$^\alpha$-[N-[N-{2-(N-Isobutyryl-N-methylamino)ethyl} -N-methylaminocarbonyl] -L-phenylalanyl]-N$^\alpha$-methyl-L-histidyl] amino-1-cyclohexyl-3-hydroxy-5-methylhexane hydrochloride Rf: 0.64 (10% methanol in chloroform)

(9) (2S,3S)-2-[N$^\alpha$-[N-[N-Methyl-N-{2-(N-thiomorpholinocarbonyl-N-methylamino)ethyl} aminocarbonyl]-L-phenylalanyl] -N$^\alpha$-methyl-L-histidyl]amino-1-cyclohexyl-3-hydroxy-5 -ethylheptane hydrochloride Rf: 0.40 (chloroform:methanol, 10:1, V/V)

(10) (2S,3S)-2-[N$^\alpha$-[N-[N-Methyl-N-{2-(N-morpholinocarbonyl-N-methylamino)ethyl}aminocarbonyl]-L-phenylalanyl] -N$^\alpha$-methyl-L-histidyl]amino-1-cyclohexyl- 3-hydroxy-5-ethylheptane hydrochloride Rf: 0.34 (chloroform:methanol, 10:1, V/V)

(11) (2S,3S)-2-[N$^\alpha$-[N-[N-{2-(N-Isobutyryl-N-methylamino)ethyl} -N-methylaminocarbonyl]-L-phenylalanyl]-N$^\alpha$-methyl-L-histidyl] amino-1-cyclohexyl-3-hydroxy-5-ethylheptane hydrochloride Rf: 0.36 (chloroform:methanol, 10:1, V/V)

(12) (2S,3S)-2-[N$^\alpha$-[N-[N-{2-[N-Hexahydro-1H-azepin-1 -ylcarbonyl)-N-methylamino] ethyl}-N-methylaminocarbonyl] -L-phenylalanyl]-N$^\alpha$-methyl-L-histidyl]amino- 1-cyclohexyl-3-hydroxy-5-ethylheptane hydrochloride Rf: 0.42 (chloroform:methanol, 10: 1, V/V)

(13) (2S,3S)-2-[N$^\alpha$-[N-[N-{2-[N-(Octahydroazocin-1-ylcarbonyl)-N-methylamino] -ethyl}-N-methylaminocarbonyl] -L-phenylalanyl]-N$^\alpha$-methyl-L-histidyl] amino- 1-cyclohexyl-3-hydroxy-5-ethylheptane hydrochloride Rf: 0.43 (chloroform:methanol, 10:1, V/V)

(14) (2S,3S)-2-N$^\alpha$-[N-[N-Methyl-N} 2-(N-thiomorpholinocarbonyl-N-methylamino)ethyl}aminocarbonyl] -L-phenylalanyl]-N$^\alpha$-methyl-L-histidyl]amino-1-cyclohexyl- 3-hydroxy-5,5-dimethylhexane hydrochloride Rf: 0.41 (chloroform:methanol, 10:1, Y/V)

(15) (2S,3S)-2-[N$^\alpha$-[N-[N-Methyl-N-(2-morpholinocarbonylethyl)aminocarbonyl] -L-phenylalanyl]-N$^\alpha$-methyl-L-histidyl] amino-1-cyclohexyl-3-hydroxy-5-ethylheptane hydrochloride Rf: 0.37 (chloroform:methanol:acetic acid, 8:1:1, V/V)

(16) (2S,3S)-2-[N$^\alpha$-[N-[N-Methyl-N-(2-morpholinocarbonylethyl)aminocarbonyl] -L-phenylalanyl]-N$^\alpha$-methyl-L-histidyl] amino-1-cyclohexyl-3-hydroxy-5-methylhexane hydrochloride Rf: 0.33 (chloroform:methanol:acetic acid, 8:1:1, V/V)

(17) (2S,3S)-2-[N$^\alpha$-[N-[N-{2-[N-(Octahydroazocin-1-ylcarbonyl)-N-methylamino]ethyl}-N-methylaminocarbonyl] -L-phenylalanyl]-N$^\alpha$-methyl-L-histidyl]amino-1-cyclohexyl-3-hydroxy-6-methylheptane hydrochloride Rf: 0,47 (chloroform:methanol, 10:1, V/V)

(18) (2S, 3S)-2-[N$^\alpha$-[N-[N-[2-(N-Dipropylcarbamoyl-N-methylamino)ethyl] -N-methylaminocarbonyl]-L-phenylalanyl] -N$^\alpha$-methyl-L-histidyl]amino-1-cyclohexyl-3-hydroxy-6-methylheptane hydrochloride Rf: 0.44 (chloroform:methanol, 10:1, V/V)

(19) (2S,3S)-2-[N$^\alpha$-[N-[N-[2-[N-(1,2,3,4-Tetrahydro-2-isoquinolylcarbonyl)-N-methylamino] ethyl]-N-methylaminocarbonyl] -L-phenylalanyl]-N$^\alpha$-methyl-L-histidyl] amino-1-cyclohexyl-3-hydroxy-6-methylheptane hydrochloride Rf: 0.43 (chloroform:methanol, 10:1, V/V)

(20) (2S,3S)-2-[N$^\alpha$-[N-[N-(2-Pyridyl)ethyl-N-methylaminocarbonyl] -L-phenylalanyl]-N$^\alpha$-methyl-L-histidyl]amino- 1-cyclohexyl-3-hydroxy-6-methylheptane dihydrochloride Rf: 0.35 (chloroform:methanol, 10:1, V/V)

(21) (2S,3S)-2-[N$^\alpha$-[N-[N-Methyl-N-{2-(N-thiomorpholinocarbonyl-N-methylamino)ethyl}aminocarbonyl]-L-phenylalanyl] -N$^\alpha$-methyl-L-histidyl]amino-1,4-dicyclohexyl- 3-hydroxybutane hydrochloride Rf: 0.38 (chloroform:methanol, 10:1, V/V)

(22) (2S,3S)-2-[N$^\alpha$-[N-[N-Methyl-N-{2-(N-thiomorpholinocarbonyl-N-methylamino)ethyl} aminocarbonyl]-L-phenylalanyl]-N$^\alpha$-methyl-L-histidyl]amino-3-hydroxy- 1,5,5-tricyclohexylpentane hydrochloride Rf: 0.5 (chloroform:methanol, 9:1, V/V)

(23) (2S,3S)-2-[N$^\alpha$-[N-[N-Methyl-N-{2-(N-thiomorpholinocarbonyl-N-methylamino)ethyl}aminocarbonyl]-L-phenylalanyl] -N$^\alpha$-methyl-L-histidyl]amino-1-cyclohexyl- 5,5-diphenyl-3-hydroxypentane hydrochloride Rf: 0.4 (chloroform:methanol, 9:1, V/V)

(24) (2S,3S)-2-[N$^\alpha$-[N-[N-Methyl-N-{2-(N-morpholinocarbonyl-N-methylamino)ethyl}aminocarbonyl]-L-phenylalanyl] -N$^\alpha$-methyl-L-histidyl]amino-1-cyclohexyl- 3-hydroxy-5-methylhexane sulfate Rf: 0.33 (10% methanol in chloroform)

(25) (2S,3S)-2-[N$^\alpha$-[N-[N-Methyl-N-{2-(N-morpholinocarbonyl-N-methylamino)ethyl}aminocarbonyl]-L-phenylalanyl]-N$^\alpha$-methyl-L-histidyl]amino-1-cyclohexyl-3-hydroxy-5-methylhexane methanesulfonate Rf: 0.33 (10% methanol in chloroform)

(26) (2S,3S)-2-[N$^\alpha$-[N-[N-Methyl-N-{2-(N-morpholinocarbonyl-N-methylamino)ethyl}aminocarbonyl]-L-phenylalanyl] -N$^\alpha$-methyl-L-histidyl]amino-1-cyclohexyl- 3-hydroxy-5-methylhexane benzenesulfonate Rf: 0.33 (10% methanol in chloroform)

EXAMPLE 5

To a solution of (2S)-2-[N-[2-(N-methyl-N-morpholinocarbonylamino)ethyl] -N-methylaminocarbonyl]oxy-3-phenylpropionic acid (216 mg) in methylene chloride (3 ml) was added oxalyl chloride (0.053 ml) at 0° C. After being stirred at the same temperature for 30 minutes, the solution was added to a solution of (2S,3S)-2-(N$^\alpha$-methyl-N$^{im}$-tosyl-L-histidyl)amino-1-cyclohexyl-3-hydroxy- 5-ethylheptane (250 mg) and N-methylmorpholine (122 mg) in methylene chloride (3 ml) at 0° C. After being stirred at the same temperature for 30 minutes, the solution was concentrated in vacuo. The residue was dissolved in ethyl acetate and the solution was washed with 5% hydrochloric acid, saturated sodium bicarbonate solution, and saturated sodium chloride solution successively, dried over anhydrous magnesium sulfate, and concentrated under reduced pressure. The residue was dissolved in N,N-dimethylformamide (5 ml). To this solution was added pyridine hydrochloride at ambient temperature and the mixture was stirred at the same temperature for 5 hours. After evaporation of the solvent, the residue was dissolved in ethyl acetate. The solution was washed with saturated sodium chloride solution, saturated sodium bicarbonate solution, and saturated sodium chloride solution successively, dried over anhydrous magnesium sulfate, and concentrated under reduced pressure. The residue was purified with silica gel thin layer chromatography (chloroform:methanol, 10:1, V/V) to give (2S,3S)-2-[N$^\alpha$-[(2S)-2-[N-[2-(N-methyl-N-morpholinocarbonylamino)ethyl]-N-methylaminocarbonyl] oxy-3-phenylpropionyl]-N$^\alpha$-methyl-L-histidyl] amino-1-cyclohexyl-3-hydroxy-5-ethylheptane (57.9 mg) as an amorphous powder. Rf: 0.28 (methanol:chloroform, 1:10, V/V)

EXAMPLE 6

The following compounds were obtained according to a similar manner to that of Example 5.

(1) (2S,3S)-2-[N$^\alpha$-[(2S)-2-[N-[2-(N-Methyl-N-morpholinocarbonylamino)ethyl]-N-methylaminocarbonyl]oxy-3-phenylpropionyl]-N$^\alpha$-methyl-L-histidyl]amino-1-cyclohexyl- 3-hydroxy-5-methylhexane Rf: 0.40 ( 10% methanol in chloroform)

(2) (2S,3S)-2-[N$^\alpha$-[(2S)-2-[N-[2-(N-Isobutyryl-N-methylamino)ethyl]-N-methylaminocarbonyl]oxy-3-phenylpropionyl]-N$^\alpha$-methyl-L-histidyl]amino-1-cyclohexyl-3-hydroxy-5-ethylheptane Rf: 0.32 (methanol:chloroform, 1:10, V/V)

(3) (2S,3S)-2-[N$^\alpha$-[(2S)-2-[N-[2-(N-Methyl-N-thiomorpholinocarbonylamino)ethyl]-N-methylaminocarbonyl] oxy-3-phenylpropionyl]-N$^\alpha$-methyl-L-histidyl] amino-1-cyclohexyl-3-hydroxy-5-ethylheptane Rf: 0.31 (chloroform:methanol, 10:1, V/V)

(4) (2S,3S)-2-[N$^\alpha$-[(2S)-2-[N-[2-{N-(Hexahydro-1H-azepin-1-ylcarbonyl)-N-methylamino}ethyl]-N-methylaminocarbonyl] oxy-3-phenylpropionyl]-N$^\alpha$-methyl-L-histidyl] amino-1-cyclohexy-3-hydroxy-5-ethylheptane Rf: 0.34 (chloroform:methanol, 10:1, V/V)

EXAMPLE 7

To a solution of (2S,3S)-2-[N$^\alpha$-[(2S)-2-[N-[2 -(N-methyl-N-morpholinocarbonylamino)ethyl]-N-methylaminocarbonyl] oxy-3-phenylpropionyl]-N$^\alpha$-methyl-L-histidyl]-amino-1-cyclohexyl-3-hydroxy-5-ethylheptane (52.9 mg) in ethanol (1 ml), which was cooled to 0° C., was added 4N solution of hydrogen chloride in ethyl acetate (17.2 μl). After being stirred at the same temperature for 5 minutes, the solution was concentrated under reduced pressure to give (2S,3S)-2-[N$^\alpha$-[(2S)-2-[N-[2-(N-methyl-N-morpholinocarbonylamino)ethyl]-N-methylaminocarbonyl]oxy-3phenylpropionyl] -N$^\alpha$-methyl-L-histidyl]amino-1-cyclohexyl-3-hydroxy-5-ethylheptane hydrochloride (55.4 mg) as an amorphous powder. Rf: 0.28 (methanol:chloroform, 1:10, V/V)

EXAMPLE 8

The following compounds were obtained according to a similar manner to that of Example 7.

(1) (2S,3S)-2-[N$^\alpha$-[(2S)-2-[N-[2-(N-Methyl-N-morpholinocarbonylamino)ethyl] -N-methylaminocarbonyl] oxy-3-phenylpropionyl] -N$^\alpha$-methyl-L-histidyl]amino-1-cyclohexyl- 3-hydroxy-5-methylhexane hydrochloride Rf : 0.40 ( 10% methanol in chloroform)

(2) (2S,3S)-2-[N$^\alpha$-[(2S)-2-[N-[2-(N-Isobutyryl-N-methylamino)ethyl] -N-methylaminocarbonyl]oxy-3-phenylpropionyl] -N$^\alpha$-methyl-L-histidyl]amino-1-cyclohexyl- 3-hydroxy-5-ethylheptane hydrochloride Rf: 0.32 (methanol:chloroform, 1:10, V/V)

(3) (2S,3S)-2-[N$^\alpha$-[(2S)-2-[N-[2-(N-Methyl-N-thiomorpholinocarbonylamino)ethyl]-N-methylaminocarbonyl] oxy-3-phenylpropionyl]-N$^\alpha$-methyl-L-histidyl] amino-1-cyclohexyl-3-hydroxy-5-ethylheptane hydrochloride Rf: 0.31 (chloroform:methanol, 10:1, V/V)

(4) (2S,3S)-2-[N$^\alpha$-[(2S)-2-[N-[2-{N-(Hexahydro-1H-azepin- 1-ylcarbonyl-N-methylamino}ethyl]-N-methylaminocarbonyl] oxy-3-phenylpropionyl]-N$^\alpha$-methyl-L-histidyl] amino-1-cyclohexyl-3-hydroxy-5-ethylheptane hydrochloride Rf: 0.34 (chloroform:methanol, 10:1, V/V)

EXAMPLE 9

To a solution of N-[N-[2-(N-morpholinocarbonyl-N-methylamino)ethyl] -N-methylaminocarbonyl]-L-phenylalanine (166 mg) and (2S,3S)-2-(N$^\alpha$-methyl-N$^{im}$tosyl-L-histidyl)amino-1-cyclohexyl-3-hydroxy-5-methylhexane (200 mg) in methylene chloride (10 ml) which was cooled to 0° C., was added 1-ethyl-3-(3-dimethylaminopropyl)carbodiimide hydrochloride (89 mg). The mixture was stirred at the same temperature for 5 hours. After evaporation of the solvent, the residue was dissolved in ethyl acetate (20 ml) and the solution was washed with 5% hydrochloric acid, 1M sodium bicarbonate solution, and brine, dried over magnesium sulfate, and concentrated under reduced pressure. After the residue was dissolved in N,N-dimethylformamide (10 ml), pyridine hydrochloride (446 mg) was added to the solution at ambient temperature. The mixture was stirred at the same temperature for 2 hours. After evaporation of the solvent, the residue was dissolved in ethyl acetate (20 ml) and the solution was washed with 1M sodium bicarbonate solution and brine, dried over magnesium sulfate, and concentrated under reduced pressure. The residue was purified with silica gel thin layer chromatography (chloroform:methanol, 9:1, V/V) to give (2S,3S)-2-[N$^\alpha$-[N-[N-methyl-N-{2-(N-morpholinocarbonyl-N-methylamino)ethyl} aminocarbonyl]-L-phenylalanyl]-N$^\alpha$-methyl-L-histidyl]amino-1-cyclohexyl-3-hydroxy- 5-methylhexane (210 mg) as an amorphous powder. Rf: 0.33 (10% methanol in chloroform) FAB-MS: 739 (M+H)$^+$

EXAMPLE 10

To a solution of (2S,3S)-2-[N$^\alpha$-[N-[N-methyl-N-{2 -(N-morpholinocarbonyl-N-methylamino)ethyl}aminocarbonyl] -L-phenylalanyl]-N$^\alpha$-methyl-L-histidyl]amino-1-cyclohexyl-3-hydroxy- 5-methylhexane (210 mg) in ethanol (10 ml), which was cooled to 0° C., was added a solution of 4M hydrogen chloride in ethyl acetate (71 μl). After being stirred at the same temperature for 5 minutes, the solution was concentrated under reduced pressure to give (2S,3S)-2-[N$^\alpha$-[N-[N-methyl-N-{2-(N-morpholinocarbonyl-N-methylamino)ethyl} aminocarbonyl]-L-phenylalanyl]-N$^\alpha$-methyl-L-histidyl] amino-1-cyclohexyl-3-hydroxy-5-methylhexane hydrochloride (216 mg) as an amorphous powder. Rf: 0.33 (10% methanol in chloroform)

EXAMPLE 11

To a solution of N-[N-{2-(N-morpholinocarbonyl-N-methylamino)ethyl} -N-methylaminocarbonyl]-L-phenylalanine (140 mg) and (2S,3S)-2-(N$^\alpha$-methyl-N$^{im}$-tosyl-L-histidyl)amino-1-cyclohexyl-3-hydroxy-6-methylheptane (190 mg) in dry methylene chloride (20 ml), which was cooled at 0° C., was added N-ethyl-N'-(3-dimethylaminopropyl)carbodiimide hydrochloride (82 mg). The mixture was stirred at the same temperature for 2 hours and then stirred at 5° C. overnight. After evaporation of the solvent, the residue was dissolved in ethyl acetate (20 ml). The solution was washed with 5% hydrochloric acid, 1M sodium bicarbonate solution and brine successively, dried over sodium sulfate, and concentrated under reduced pressure to give (2S,3S)-2-[N$^\alpha$-[N-[N-methyl-N-{2-(N-morpholinocarbonyl-N-methylamino)ethyl}aminocarbonyl]-L-phenylalanyl]-N$^\alpha$-methyl-N$^{im}$-tosyl-L-histidyl]amino-1-cyclohexyl-3-hydroxy- 6-methylheptane. After the residue was dissolved in N,N-dimethylformamide (20 ml), pyridine hydrochloride (401 mg) was added to the solution at ambient temperature. The mixture was stirred at the same temperature for 2 hours. After evaporation of the solvent, the residue was dissolved in ethyl acetate (20 ml). The solution was washed with brine, 1M sodium bicarbonate solution and brine, successively, dried over magnesium sulfate, and concentrated under reduced pressure. The residue was purified with silica gel thin layer chromatography (chloroform:methanol, 9:1, V/V) to give (2S,3S)-2-[N$^\alpha$-[N-[N-methyl-N-{2-(N-morpholinocarbonyl-N-methylamino)ethyl} aminocarbonyl]-L-phenylalanyl]-N$^\alpha$-methyl-L-histidyl] amino-1-cyclohexyl-3-hydroxy-6-methylheptane (203 mg) as an amorphous powder. mp: 89°–92° C. Rf: 0.51 (10% methanol in chloroform)

What we claim is:

1. A compound having the formula:

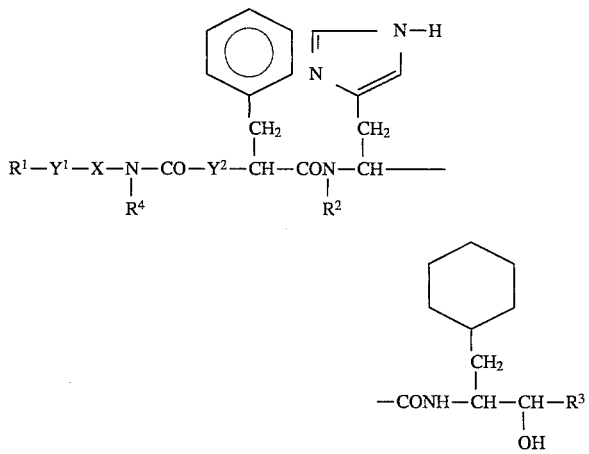

wherein R$^1$ is morpholinocarbonyl or thiomorpholinocarbonyl;

R$^2$ is methyl;

R$^3$ is isobutyl or 2-ethylbutyl;

R$^4$ is methyl;

X is ethylene;

Y$^1$ is a single bond or

wherein R⁵ is methyl; and

Y² is —NH—; or its pharmaceutically acceptable salt.

2. A compound having the formula:

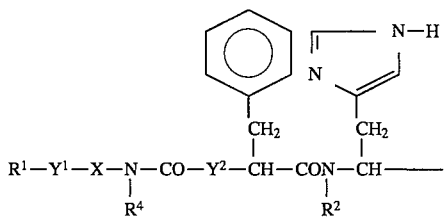

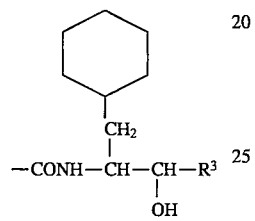

wherein R¹ is selected from the group consisting of morpholinocarbonyl, thiomorpholinocarbonyl, piperidinocarbonyl, hexahydro-1H-azepin-1-ylcarbonyl, dipropylcarbamoyl, 1,2,3,4-tetrahydro-2-isoquinolylcarbonyl and pyridyl;

R² is lower alkyl

R³ is selected from the group consisting of lower alkyl and cyclo(lower) alkyl substituted lower alkyl;

R⁴ is lower alkyl;

X is lower alkylene;

Y¹ is a single bond or

wherein R⁵ is lower alkyl; and

Y² is —NH—; or its pharmaceutically acceptable salt.

3. A compound having the formula:

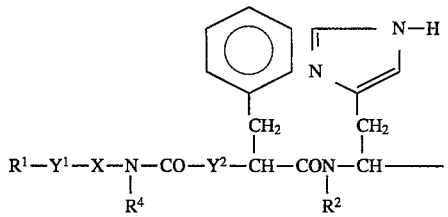

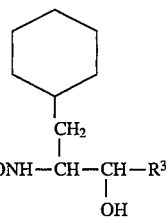

wherein R¹ is selected from the group consisting of morpholinocarbonyl, thiomorpholinocarbonyl, piperidinocarbonyl, hexahydro-1H-azepin-1-ylcarbonyl, di(lower) alkylcarbamoyl, 1,2,3,4-tetrahydro-2-isoquinolylcarbonyl, lower alkanoyl and pyridyl;

R² is lower alkyl

R³ is selected from the group consisting of lower alkyl and cyclo (lower) alkyl substituted lower alkyl;

R⁴ is lower alkyl;

X is lower alkylene;

Y¹ is a single bond or

wherein R⁵ is lower alkyl; and

Y² is —NH—; or its pharmaceutically acceptable salt.

4. A compound according to claim 3, wherein R³ is lower alkyl, and

Y² is —NH—.

5. A compound of claim 1, which is (2S,3S)-2-[Nα-[N-[N-methyl-N-{2-(N-morpholinocarbonyl-N-methylamino) ethyl} aminocarbonyl]-L-phenylalanyl]-Nα-methyl-L-histidyl]amino-1-cyclohexyl- 3-hydroxy-5-methylhexane, its hydrochloride, its sulfate, its methanesulfonate or its benzenesulfonate.

6. A compound of claim 1, which is (2S,3S)-2-[Nα-[N-[N-methyl-N-{2-(N-thiomorpholinocarbonyl-N-methylamino)ethyl} aminocarbonyl]-L-phenylalanyl] -Nα-methyl-L-histidyl]amino-1-cyclohexyl- 3-hydroxy-5-methylhexane or its hydrochloride.

7. A compound of claim 1, which is (2S,3S)-2-[Nα-[N-[N-methyl-N-{2-(N-morpholinocarbonyl-N-methylamino) ethyl} aminocarbonyl]-L-phenylalanyl] -Nα-methyl-L-histidyl]amino-1-cyclohexyl- 3-hydroxy-5-ethylheptane or its hydrochloride.

8. A compound of claim 1, which is (2S,3S)-2-[Nα-[N-[N-methyl-N-(2-morpholinocarbonylethyl)aminocarbonyl] -L-phenylalanyl]-Nα-methyl-L-histidyl]amino-1-cyclohexyl-3-hydroxy-5-ethylheptane or its hydrochloride.

9. A pharmaceutical composition comprising a compound of claim 3, as an active ingredient, in association with a pharmaceutically acceptable, nontoxic carrier or excipient.

10. A method for the therapeutic treatment of hypertension in a patient in need thereof which comprises administering a compound of claim 3 to human beings or animals.

11. A method for the therapeutic treatment of heart failure in a patient in need thereof which comprises administering a compound of claim 3 to human beings or animals.

* * * * *